(12) United States Patent  
Moynihan et al.

(10) Patent No.: US 12,379,317 B2
(45) Date of Patent: Aug. 5, 2025

(54) READER DEVICE FOR LUMINESCENT IMMUNOASSAYS

(71) Applicant: Biosensia Patents Limited, Dublin (IE)

(72) Inventors: Shane Moynihan, Dublin (IE); Diarmuid Flavin, Dublin (IE)

(73) Assignee: Biosensia Patents Limited, Dublin (IE)

( * ) Notice: Subject to any disclaimer, the term of this patent is extended or adjusted under 35 U.S.C. 154(b) by 51 days.

(21) Appl. No.: 17/465,049

(22) Filed: Sep. 2, 2021

(65) Prior Publication Data

US 2022/0128472 A1 Apr. 28, 2022

Related U.S. Application Data

(63) Continuation of application No. 16/028,665, filed on Jul. 6, 2018, now abandoned, which is a continuation of application No. 14/234,136, filed as application No. PCT/IB2012/001907 on Jul. 20, 2012, now abandoned.

(60) Provisional application No. 61/510,779, filed on Jul. 22, 2011.

(51) Int. Cl.
*G01N 21/64* (2006.01)
*G01N 33/53* (2006.01)
*G01N 21/27* (2006.01)

(52) U.S. Cl.
CPC ....... *G01N 21/6486* (2013.01); *G01N 21/645* (2013.01); *G01N 33/5302* (2013.01); *G01N 21/278* (2013.01); *G01N 2021/6419* (2013.01); *G01N 2021/6421* (2013.01); *G01N 2021/6441* (2013.01); *G01N 21/6452* (2013.01); *G01N 2021/6471* (2013.01); *G01N 2201/0624* (2013.01); *G01N 2201/0627* (2013.01); *G01N 2201/0648* (2013.01); *G01N 2201/0693* (2013.01)

(58) Field of Classification Search
None
See application file for complete search history.

(56) References Cited

U.S. PATENT DOCUMENTS

| 5,573,950 A * | 11/1996 | Graessle | C12M 23/04 422/561 |
| 5,851,488 A | 12/1998 | Saul et al. | |
| 6,267,722 B1 * | 7/2001 | Anderson | G16H 15/00 436/814 |
| 6,707,554 B1 | 3/2004 | Miltner et al. | |

(Continued)

FOREIGN PATENT DOCUMENTS

| JP | S62-140350 A | 6/1987 |
| JP | 2002-525625 A | 8/2002 |

(Continued)

OTHER PUBLICATIONS

International Search Report for PCT/IB2012/001907, dated Jan. 28, 2013, published as WO 2013/014540 (5 pages).

(Continued)

*Primary Examiner* — Neil N Turk
(74) *Attorney, Agent, or Firm* — Choate, Hall & Stewart LLP; Brian E. Reese; Ronen Adato

(57) ABSTRACT

The present disclosure, among other things, describes a reader system comprising a casing, an optical system, an electromechanical motor system, and one or more digital processors.

13 Claims, 19 Drawing Sheets

Reader optical-path schematic – top view.

(56) References Cited

U.S. PATENT DOCUMENTS

| | | | |
|---|---|---|---|
| 7,217,573 B1* | 5/2007 | Oshida | G01N 21/6428 |
| | | | 435/6.12 |
| 8,323,566 B2 | 12/2012 | Murakami et al. | |
| 2004/0017150 A1* | 1/2004 | Fricke | G01N 21/6452 |
| | | | 313/501 |
| 2007/0233399 A1 | 10/2007 | Yonezawa | |
| 2008/0131977 A1* | 6/2008 | Rosenstein | G01N 33/558 |
| | | | 382/128 |
| 2010/0264332 A1 | 10/2010 | Coker et al. | |
| 2011/0022324 A1 | 1/2011 | Knopp et al. | |
| 2019/0003974 A1 | 1/2019 | Moynihan et al. | |

FOREIGN PATENT DOCUMENTS

| | | |
|---|---|---|
| JP | 2003-185666 A | 7/2003 |
| JP | 2007-183257 A | 7/2007 |
| JP | 2007-537453 A | 12/2007 |
| WO | WO-2005/114142 A2 | 12/2005 |
| WO | WO-2010/021088 A1 | 2/2010 |
| WO | WO-2010/105802 A2 | 9/2010 |
| WO | WO-2010/120951 A1 | 10/2010 |
| WO | WO-2013/014540 A2 | 1/2013 |

OTHER PUBLICATIONS

Written Opinion for PCT/IB2012/001907, dated Jan. 28, 2013, published as WO 2013/014540 (13 pages).

* cited by examiner

```
------------------------------------
Date:            31 May 2011 11:03
Patient ID:      JOE.SMITH
Test Batch ID:   226
Operator:        USER.123
Reader Serial #: R000217220A Batch Cal Date:  11 Jan 2011
System QC Date:  31 May 2011

1. THC              Negative
2. MDMA             Negative
3. Methamphetamine  Negative
4. Cocaine          Negative
5. LSD              Negative
6. Opiate           Negative

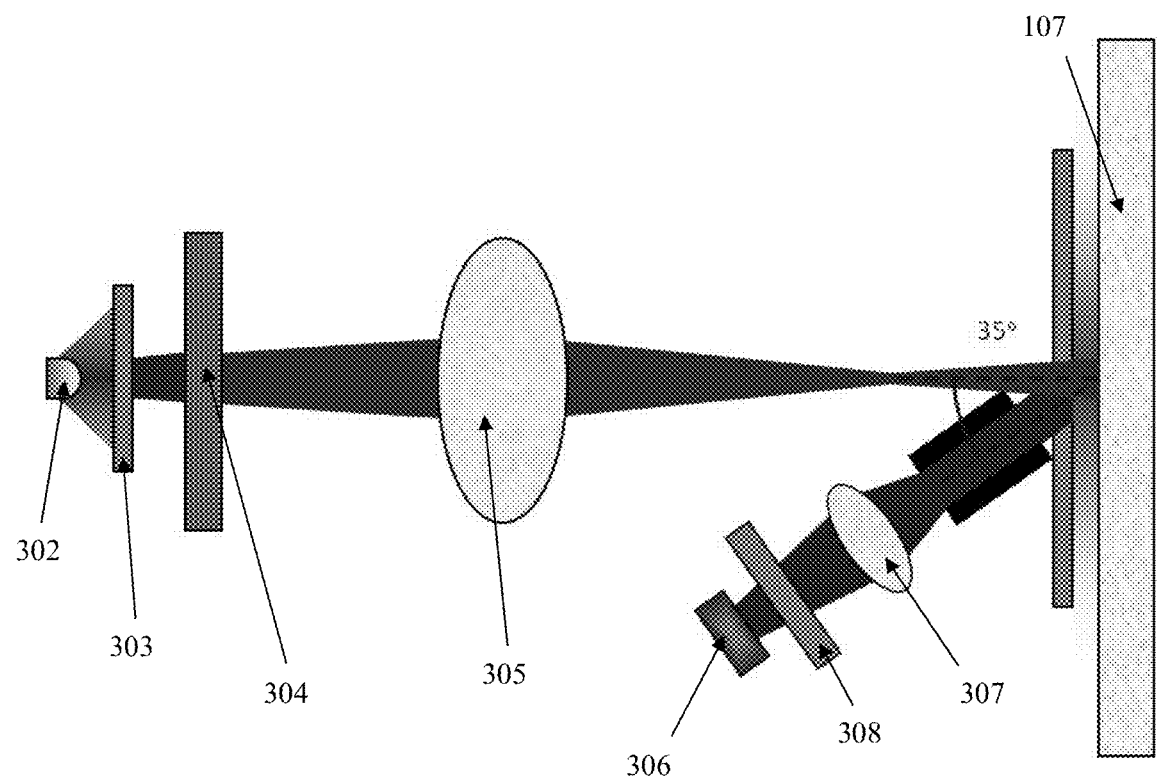
Figure 15 (a): Reader optical-path schematic – side view.

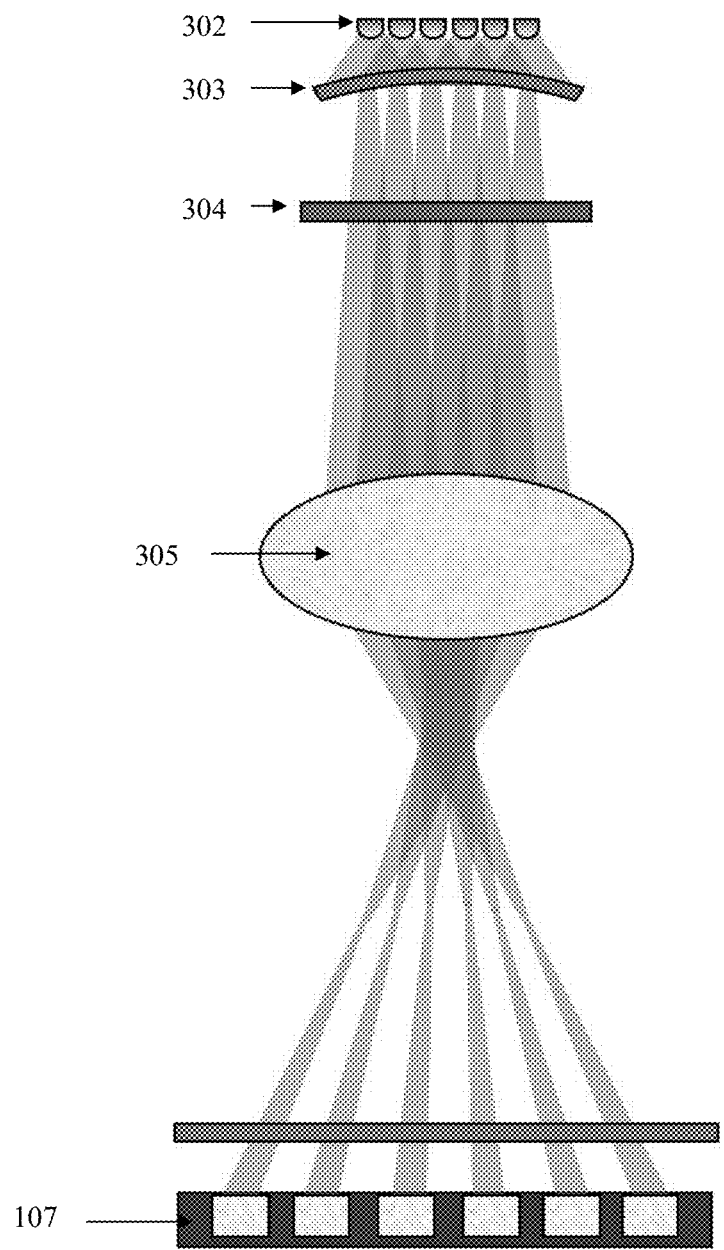
Figure 15 (b): Reader optical-path schematic – top view.

READER DEVICE FOR LUMINESCENT IMMUNOASSAYS

CROSS-REFERENCE TO RELATED APPLICATIONS

This application is a continuation of U.S. application Ser. No. 16/028,665, filed Jul. 6, 2018, which is a continuation of U.S. application Ser. No. 14/234,136, filed Jan. 21, 2014. U.S. application Ser. No. 14/234,136 is a national stage entry of PCT/IB12/01907, filed Jul. 20, 2012, which claims priority to U.S. provisional application Ser. No. 61/510,779, filed Jul. 22, 2011, the entirety of which is hereby incorporated by reference.

BACKGROUND

Immunoassays may be used for the determination of clinical decisions. As such, accuracy, reliability, and repeatability of immunoassay interpretation are largely important. With regard to the field of use, this analysis is important in a point-of-care or mobile setting. In these settings, tests may be carried out by unskilled technicians or patients themselves, while still requiring the maintenance of traceability and accuracy. In addition, communication of test and auditing data is important; insofar as it may be, for example, examined by remote healthcare professionals, integrated with hospital LIMS systems, or used to verify device operation.

SUMMARY OF CERTAIN EMBODIMENTS

Various embodiments of the present invention utilize photoluminescence based methodologies to provide accurate, non-subjective interpretation of labelled mobilizable reagent binding in immunoassays, and quantization of analyte presence or concentration in fluid test samples. Bespoke algorithms and devices compensate for assay and optical variability. Embodiments of the invention combine portability, automation and communication technologies to cater for use by an unskilled technician in a point-of-care setting.

Embodiments of the present invention concern an immunoassay analysis system for the recording and interpretation of photoluminescent immunoassays, herein termed the reader system. Embodiments of the invention quantify photoluminescence from one or more capture zones of an immunoassay, and thereby determines a quantitative or qualitative measurement of analyte presence within a fluid sample.

In brief, a reader system according to embodiments of the present invention may comprise a casing, an optical system, an electromechanical motor system, and one or more digital processors. The casing may include at least one port leading to a holster which is configured to receive a cartridge comprising a vertically oriented immunoassay device for analyzing one or more analytes in a fluid sample. The optical system may include excitation optics comprising a light source and an excitation lens configured to transmit light from the light source and thereby excite a region of the vertically oriented immunoassay device when a cartridge is placed in the holster, and collection optics comprising a photosensor and a collection lens configured to collect emitted light from the vertically oriented immunoassay device when a cartridge is placed in the holster. The electromechanical motor system may be configured to move the holster in a vertical direction with respect to the optical system so that the optical system can interrogate different regions of the vertically oriented immunoassay device when a cartridge is placed in the holster. The one or more digital processors may be associated electronics configured to receive data from and control the optical system and to control the electromechanical motor system A reader system, in some embodiments, includes non-volatile or volatile digital memory for storing data generated by the optical system.

In some embodiments, the casing of a reader system further includes a display screen, a data entry device, such as a keypad or display integrated touch-screen, or a combined device that acts as a display screen and a data entry device.

In some embodiments, a light source is a light emitting diode (LED) surface mounted device. The light source may also include integrated lens for collimation of LED emitted light. In some embodiments, a reader system includes multiple excitation sources, for example, LEDs with various central emission wavelengths, with matched optical filters.

In some embodiments, excitation optics includes an plate (e.g., absorptive or reflective plate) with an optical aperture. The aperture may be aligned within the optical excitation path; and defined to form a specific, regular excitation area upon the immunoassay device. In an implementation, a excitation area is 0.3 mm-3 mm in width and 0.2 mm to 2 mm in height.

In some embodiments, a collection lens collects emitted light from an entire excited region. The collection lens may integrate the emitted light and direct it onto the central portion of a corresponding photosensor for detection.

In some embodiments, excitation or collection optics each includes an optical filter. For example, the optical filer can be a band-pass or short-pass optical filer. The optical filer may operate by interference or by absorption. An optical filter in the excitation optics tunes optical excitation wavelengths experienced by an immunoassay. An optical filter in the collection optics passes wavelengths associated with the photoluminescent label emission of an immunoassay, while blocking wavelengths associated with optical excitation. Additionally or alternatively, an optical collection filter may be mechanically actuated.

In some embodiments, a cartridge comprising a vertically oriented immunoassay device is located within a holster. The vertically oriented immunoassay device may include one or multiple parallel, vertically oriented immunoassay channels. The one or more immunoassay channels may each independently comprise one or more test lines for analyzing one or more analytes. A reader system may include multiple light sources and multiple photosensors, with one of each being dedicated to each individual immunoassay channel. The multiple light sources may each have different central wavelength. Electronic frequency filtering may be used to filer signals from the multiple photosensors. For example, electronic filtering may be applied to the photosensor signal to register signals associated with the duty cycle of immunoassay excitation and thus the immunoassay photoluminescence, while blocking low or high frequency system noise.

In certain embodiments, the pairs of light sources and photosensors are configured so that different immunoassay channels are interrogated at different points in time. In certain embodiments, the multiple immunoassay channels are spatially separated such that cross talk between different immunoassay channels and different photosensors is substantially absent when the multiple immunoassay channels are interrogated simultaneously.

In some embodiments, an aperture plate includes an aperture for each light source. There may be a dedicated collection lens associated with each immunoassay channel and photosensor. The plate may be absorptive or reflective. At least one dimension (e.g., width, or height) of each of one or more apertures is in a range of 0.1-2 mm, 0.7-0.8 mm, or 0.3-0.4 mm.

In some embodiments, optical emission intensity of the light source is controlled and stabilised through a cartridge scan. In this case, the excitation optics may include a dedicated excitation source monitoring photosensor. The light source emission intensity can be monitored by analysis of the monitoring photosensor electronic signal. Feedback of this monitoring signal to the excitation source may act to stabilize the emission of the excitation source across all scans. Feedback stabilization may be carried out throughout a scan, for each duty cycle of each light source's emission. Alternatively, feedback stabilization may be independently carried out for each light source prior to the commencement of each cartridge scan. In certain embodiments, a reader system includes a proportional-integral-derivative control algorithm to optimally stabilise light source emission at a desired intensity by analysis of the monitoring photosensor signal.

In some embodiments, there is an angular offset between the optical collection plane of the photodiode/lens assembly, and the optical excitation plane. The specific angular offset and configuration can be selected in order to inhibit direct reflection of excitation light into the detector assembly, while maintaining efficient excitation and collection. For example, the optical excitation is normal to the cartridge surface, while detection is offset by 35 degrees.

In some embodiments, one or more digital processors collect data generated when the optical system scans the vertically oriented immunoassay device. One or more digital processors can process the data to quantify an amount of one or more analytes in a fluid sample that was applied to the immunoassay device before the cartridge was placed in the holster.

For example, digital processors may use an algorithm to characterise the presence or amount of an analyte within a fluid sample, according to assay specific calibration parameters. An algorithm provides either a quantitative, semi-quantitative or qualitative estimate of analyte concentration within the fluid sample. In certain embodiment of this invention, multiple photoluminescent immunoassays assays are present in the cartridge device, and the algorithm provides independent quantitative, semi-quantitative or qualitative estimations of analyte concentration for all tested analytes within the sample.

In some embodiments, a reader system includes one or more quality controls checks that are actualised in software on the one or more digital processors. Quality controls checks may include: a quality control check of scan data, including a check of control line development; a check of channel clearance; and checks as to the size and position of peaks. Additionally, the reader software verifies the time of test as being within the expiry date of a particular assay.

In some embodiments, a reader system includes a barcode reading system. A barcode may be encoded on a cartridge. A barcode may be encoded with assay specific calibration data relating to an assay cartridge batch. Upon introduction of the cartridge to the reader system, the assay specific calibration data may be read, interpreted and copied to internal reader memory. For example, a barcode reading system may be one dimensional, or two dimensional. Exemplary information that can be encoded in a barcode reading system includes, but is not limited to, identification of cartridge type or lot data, lot manufacture and expiry dates, analyte names, cartridge expected response, lot parameters, peak finding parameters, calibration parameters, and any combination thereof.

In some embodiments, a read system includes at least one sensor for recognizing cartridge insertion or removal. The sensor may be an optical or mechanical sensor. For example, one or more optically emissive sources and corresponding optical sensors can be included. These sensors may be held within the cartridge holster, and their positioning corresponds to locations which define the cartridge insertion or removal of the cartridge. In this case, the optical sensor may be a light source and photosensor couple. This may be located in close proximity to the mouth of the holster. Upon insertion, the cartridge blocks propagation of light from the sensor light source to its corresponding photosensor. The sensor registers full removal of the cartridge by the resumption of light propagation from the sensor light source to its corresponding photosensor. A mechanical switch sensor may be located at the base of the holster. Upon full insertion of the cartridge into the holster, this switch is actuated by the cartridge, enabling the detection of cartridge insertion. In some embodiments, there exists a physically separate quality control component with substantially the same external dimensions as a cartridge. This component may include photoluminescent materials that exhibit characterised levels of photoluminescence upon excitation by the light source. For example, photoluminescent materials can be or comprise plastics impregnated with photoluminescent dyes, nanocrystals, quantum dots or any combination thereof. Generally, the photoluminescent areas of a quality control component are localised at the optical plane of the reader, at a similar position to that of immunoassay surface in a given cartridge. Further, reader scans of this quality control component may be carried out in a similar method to that of the immunoassay cartridge. Photoluminescent areas may be defined on the quality control component using masked materials, coated materials, multilayer etched materials or any combination thereof. Photoluminescent areas may be patterned such that optical misalignments within the reader system lead to predictable changes in the pattern or intensity of emitted light.

In some embodiments, the one or more digital processors of a read system collect data generated when the optical system scans the quality control component and use the data to validate the reader system for further use. The one or more digital processors may collect data generated when the optical system scans the quality control component and use the data to modify internal calibration factors of the reader system. The one or more digital processors may collect data generated when the optical system scans the quality control component and use the data to calculate a degree of optical misalignment, such as the direction and degree of lateral misalignment, degree of focus or defocus, or optical system tilt, between the optical system and the holster. In this case, the one or more digital processors may control the electro-mechanical motor system to actuate and thereby bring the optical system and the holster into optical alignment.

In some embodiments, a reader system includes travel sensors that are used to detect and report a relative position of the holster. The travel sensors may be optical or mechanical.

In some embodiments, a reader system includes a printer for the printout of hardcopies of scan results and data following the reading of an immunoassay cartridge, or data from stored memory. This printer may be incorporated within the casing of the reader device, or provided as a a separate component. In the case of the printer being a separate component, the printer may be interfaced with the reader using a USB, Ethernet or serial port connection. Power may be provided to the printer device directly from the reader system or via a separate power supply component.

In some embodiments, a reader system includes a processing algorithm for the verification of immunoassay batch responses. This algorithm analyses the response of one or more immunoassay cartridges of the specified batch, run with control liquids of specified concentrations. The algorithm compares expected responses with those found from these cartridges, and verifies the immunoassay batch as operating to a given specification. Further, this algorithm also may conduct the optimisation and correction of immunoassay batch specific calibration parameters, as stored within reader memory, to compensate for time-related changes in immunoassay photoluminescence response. In this case, following the analysis of one or more immunoassay cartridges of the specified batch, run with control liquids of specified concentrations, internal calibration parameters are then updated to provide a best-fit result to control responses.

In some embodiments, a reader system includes components and protocols for external wireless access, such as by Wi-Fi, ANT or Bluetooth. In an implementation, this connectivity enables remote reader operation diagnostics, firmware or software updates and data transfer.

In some embodiments, a reader system includes components and protocols for wired connectivity, such as by RS-232 serial, universal serial bus (USB) or Ethernet cable. In an implementation, this connectivity enables remote reader operation diagnostics, firmware or software updates and data transfer.

In some embodiments, a reader system includes alignment features within a cartridge holster. These features hold the cartridge in position and ensure that the immunoassay surface is localised at the optical plane. In certain embodiments, spring loaded dowels are located in positions corresponding to recesses in the assay cartridge when the cartridge is correctly localised within the holster. In certain embodiment, physical alignment features prevent the mis-insertion of the cartridge, by blocking full insertion of the cartridge at an incorrect rotation.

In some embodiments, a reader system includes an internal battery which supplies the reader with electrical power when not connected to a mains power supply.

In some embodiments, a reader system includes electronic memory and a digital file management system for the storage of data, operation parameters, and software and user interface details. Files stored within this electronic memory may include: Scan files, calibration files, quality control run files, user lists, settings and change logs, scan logs, calibration run logs, or user logs. In order to review a potentially large number of scan files, search functionality may be implemented. This search functionality generally consists of user interface options enabling the user to filter scans results by date, operator, patient ID or test.

The present disclosure include, among other thing, methods of using reader systems described herein.

BRIEF DESCRIPTION OF THE DRAWINGS

FIG. 13 shows an example printout of test data following a test scan.
FIGS. 15(a) and 15(b) show exemplary optical-path schematics of a reader system: (a) side view and (b) top view.

DEFINITIONS

Figure 1:
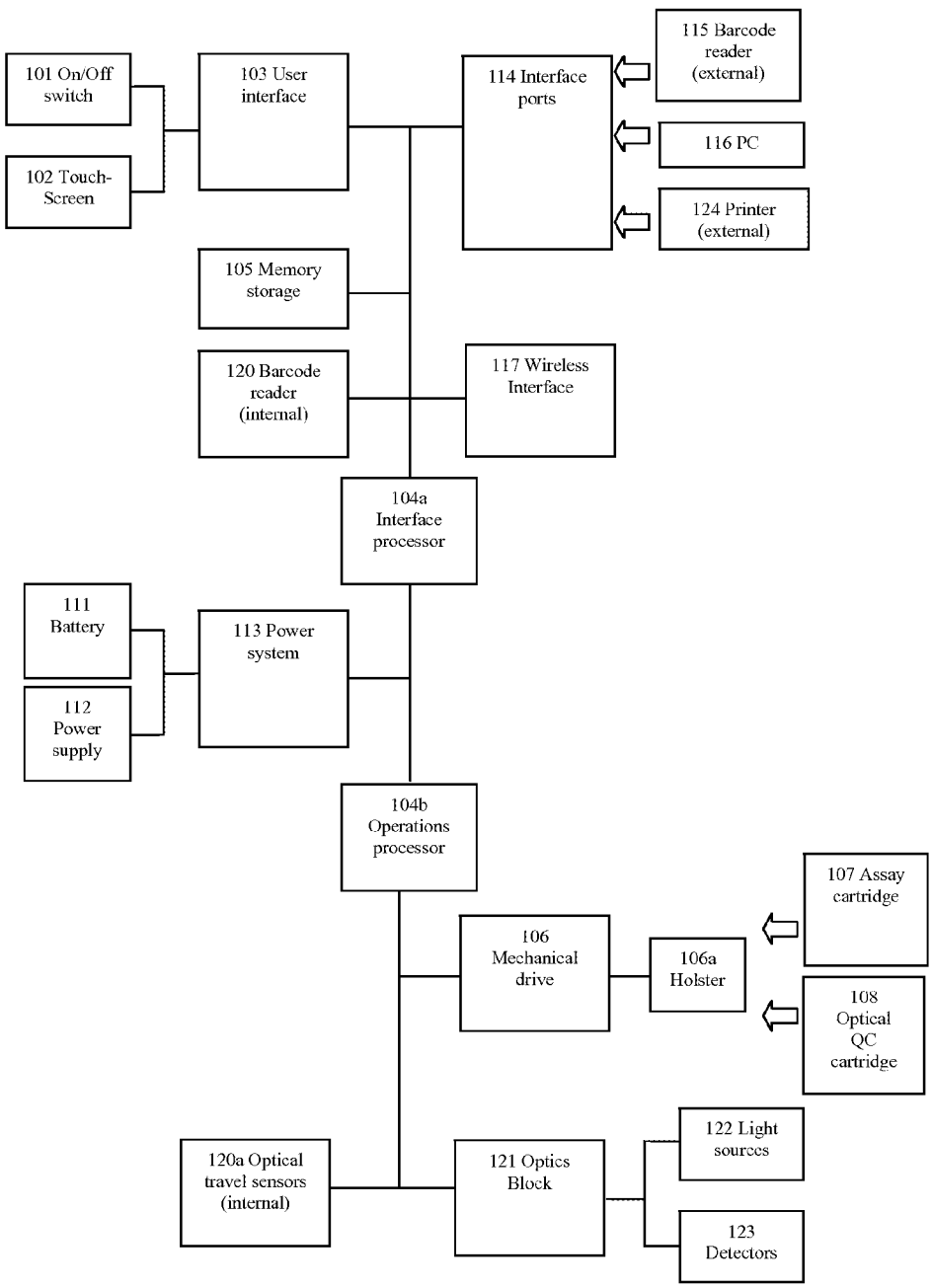
FIG. 1 shows a reader system top level diagram.

Assay—As used herein, the term "assay," refers to an in vitro analysis carried out to determine the presence or absence of one or more target analytes in a fluid sample. In certain embodiments the assay may be quantitative and determine the amount of the one or more target analytes in the fluid sample. In general, an assay includes at least one pair of reagent components where at least one of the reagent components has a high binding affinity for the other. In certain embodiments, the assay is an immunoassay (e.g., a sandwich, competitive or inhibition immunoassay). Generally, an immunoassay includes an antibody component which binds with high affinity to another antibody component or to an antigen component. In certain embodiments, the assay is a molecular assay and includes a pair of nucleic acid components which hybridize to form a complex.

Target analyte—As used herein, the term "target analyte" or "analyte" refers to the substance or substances that an assay is designed to detect. Examples of analytes include, but are not restricted to proteins (e.g., antibodies, hormones, enzymes, glycoproteins, peptides, etc.), nucleic acids (e.g., DNA, RNA, etc.), lipids, small molecules (e.g., drugs of abuse, steroids, environmental contaminants, etc.) and infectious disease agents of bacterial or viral origin (e.g., *E. coli, Streptococcus, Chlamydia*, Influenza, Hepatitis, HIV, Rubella, etc.).

DETAILED DESCRIPTION OF CERTAIN EMBODIMENTS

A reader system for the recording and interpretation of photoluminescent immunoassays is described herein in connection with embodiments of the present invention. Various embodiments of the invention quantify photoluminescence from one or more capture zones of said immunoassay, and determines a quantitative or qualitative measurement of analyte presence within a fluid sample.

In brief, a reader system may include a casing, incorporating a display screen, or a data entry device, such as a keypad or display integrated touch-screen, or a combined device that acts as a display screen and a data entry device. This casing may also incorporate a fluidic immunoassay device access port, and contains a holster receptacle for receiving an external immunoassay fluidic device. Said external immunoassay fluidic device comprises one or more immunoassays oriented in a substantially vertical configuration, configured for the analysis of a fluid sample; and is herein referred to as the cartridge. Further, the reader comprises an optical system within the casing, consisting of excitation and collection optics within a single optical block; and an electromechanical motor system, such as a stepper motor, whereby the holster is moved in a vertical direction with respect to the optical block. Also, the reader system incorporates a digital processor and electronics for the actuation and control of readings, and non-volatile digital memory for the storing of data. It is to be understood that the reader system may incorporate multiple processor components, with a division of processing occurring between separate components. For example a single processor may handle sensing and time critical tasks, while an additional processor may control screen display, user interface operations, communications, and additional processing. Additionally, the reader may incorporate communication ports or wireless connectivity, internal batteries and an internal or external printer unit (such as a thermal printer) for the printout of hardcopies of scan results following the reading of an assay, or from stored memory.

With regard to the particulars of the various reader assemblies and components, these are further detailed, below.

In some embodiments, the cartridge holster of a reader system includes alignment features to ensure the correct insertion and placement of the cartridge within the reader. In certain embodiments, spring loaded dowels are located in positions corresponding to recesses in the assay cartridge when the cartridge is correctly localised within the holster. Upon correct insertion of the cartridge, the dowels register with recesses in the cartridge. This locks the cartridge in position, and ensures that the immunoassay surface is localised at the optical plane until a force is applied to remove said cartridge. In certain embodiments, physical alignment features prevent the mis-insertion of the cartridge, by blocking insertion of the cartridge at an incorrect rotational alignment. In certain embodiments, the cartridge holster incorporates fluidic flow channels to ensure any liquid spillages from the cartridge or into the reader port flow along a defined path to a spill receiver area. This area may be upon, or otherwise connected to an additional removable cover on the underside of the reader casing, enabling access to and cleaning of this spill area without disassembly of the reader device.

In some embodiments, a reader system includes optically emissive sources and corresponding optical sensors for the recognition of cartridge insertion. These sources and sensors can generally be placed within the cartridge holster opposite the optics block. The positioning of these optical components corresponds to absorptive or reflective features upon the cartridge, generally defined on the distal surface of the cartridge to that of the assay channels. Upon insertion of the cartridge into the cartridge holster, the response registered by the optical sensors varies as light emitted by the optically emissive sources interact with the absorptive or reflective features upon the cartridge. Analysis of the sensor response during the insertion of the cartridge enables recognition of the cartridge movement direction, and verification of full cartridge insertion. Additional absorptive or reflective features may be incorporated upon the cartridge may, encoding information relating to the identification of cartridge type or immunoassay cartridge batch data. In this case, the reader may also incorporate additional optically emissive source and corresponding optical sensor components for the registration of these features. In certain embodiments, the reader system may incorporate optical or mechanical sensors, which register full cartridge insertion or removal. In this case, the reader may automatically initiate travel of the holster without further user intervention upon full cartridge insertion or removal. For example, the reader system may initiate a scan or move of the holster to a rest position, upon insertion or removal of the cartridge, respectively.

In some embodiments, a reader system includes a one dimensional or two dimensional barcode reader, as known in the art, within the reader casing. Generally, these register and read barcode structures disposed upon the assay cartridge. In an embodiment of this invention, the barcode encodes information for the identification of cartridge type or lot data. In certain embodiments, the barcode is a two dimensional barcode and encodes information corresponding to any of the following: identification of cartridge type or lot data, lot manufacture and expiry dates, analyte names, cartridge expected response, lot parameters, peak finding parameters, and calibration parameters for the immunoassay cartridge batch.

In some embodiments, a reader system includes a radio frequency identification (RFID) reader. This registers and reads RFID chips present in or on the assay cartridge. In an embodiment of this invention, the RFID chip encodes information relating to any of: identification of cartridge type or lot data, lot manufacture and expiry dates, analyte names, cartridge expected response, lot parameters, peak finding parameters, and calibration parameters for the cartridge lot.

In some embodiments, the motor component integrates an encoder system which detects and reports the relative motor actuation position. Alternatively, holster relative position may be determined by calculation from motor speed and time of travel. In each case, holster position may be determined with reference to this relative measurement and signals received from particular optical or mechanical travel sensors located relative to specific positions in the holster travel. In the case of optical travel sensors, the holster component incorporates beam blocking features, which break an optical beam sensed by the optical travel sensors, indicating holster position at these locations. Alternatively, the holster component may incorporate reflective features, which direct an optical beam to the optical travel sensors, indicating holster position at these locations.

An example reader system optical block and optical paths is schematically represented in FIGS. 15 (a) and 15 (b). In an embodiment of the present invention, the excitation optics within the optical block include: one or more light sources [302] and an excitation lens [305]. In particular embodiments of the present invention, an excitation light source may comprise any of, for example: an inorganic light emitting diode (LED), or an organic LED, or a laser. Generally, the light sources have emission wavelengths compatible with the excitation spectra of photoluminescent labels associated with the mobilizable or control reagents of the assay. In an embodiment of the present invention, optical excitation is derived from six surface mounted device LEDs, each with an integrated lens which serves to partially collimate emitted light.

Generally, one or more excitation lenses [305] are located within the light paths of excitation, and direct light source emitted optical energy to the surface of the immunoassay device. An excitation lens may also act to collimate or spread excitation light. An excitation lens may be formed of one of a variety of optically transparent materials; including glass, fused silica or organic polymers (for example: polymethylmethacrylate, polycarbonate, polytetrafluoroethylene, polystyrene, or cyclic olefin co-polymer). Generally, an excitation lens is of a light converging form, with the design of the lens being one of, for example: convex, bi convex, spherical, plano-convex, positive meniscus, or aspheric. Lens parameters include focal length, numerical aperture, material and optical coatings. These are selected to optimise the optical design and have transparency corresponding to the wavelengths of excitation.

In particular embodiments of the reader system, excitation optics incorporate an absorptive or reflective plate with one or more optical apertures [303]. The aperture plate may be coated with a stable absorptive material to ensure scattering and reflections are limited. Defined areas of stable diffusely reflective material may be further coated onto the aperture plate, causing a portion of light source emitted light to be back-reflected to light-source monitoring photosensors. Optical apertures restrict excitation light rays to those passing through the aperture. Each aperture is aligned to an optical excitation path of a single corresponding light source, and is shaped and sized to block specific light rays. An aperture forms a specific, regular excitation area upon the immunoassay device by blocking light corresponding to optical rays which would illuminate sections outside this area. The placement and size of this optical excitation area may be tuned by modifying the corresponding aperture's position and dimensions. Apertures may be designed to ensure that all excitation areas are regular and of similar size. In particular, the aperture plate may be curved, ensuring optical light paths are of similar lengths following passing through the aperture plate. In particular embodiments, apertures act to collimate the excitation light by selecting light rays originating from the central, more homogenous angles of light source emission. This may be important for subsequent optical filtering using an interference type filter, as the pass and stop bands of these filters are dependent on the angle of incidence of a light beam. In certain embodiments, apertures are 0.2 mm-2 mm in width and 0.1 mm to 1 mm in height, and each excitation area is 0.3 mm-3 mm in width and 0.2 mm to 2 mm in height.

In particular embodiments of the present invention, excitation optics also comprise one or more optical filters [304]. An optical excitation filter shapes the spectral profile of excitation light experienced by the immunoassay device. This filter may act to ensure spectral separation between excitation light and luminophore emitted light. An optical excitation filter may, for example, be of band-pass or short-pass variety, and may operate by interference or absorptive mechanisms. Generally, an excitation filter is selected such that the filter pass-band corresponds to some portion of the excitation spectrum of the photoluminescent labels associated with the mobilizable or control reagents of the assay, and that the filter stop-band corresponds to some portion of the emission spectrum of these photoluminescent labels. The Stokes' shift between a photoluminescent label's excitation and emission spectra defines the maximum filter transition band. In an embodiment, a short pass interference optical filter is selected.

Generally, collection optics include: one or more collection lenses [307] for the collection of light emitted from the immunoassay surface; and one or more photosensors [306] for the detection and transduction of this luminescence to an electrical signal.

Generally, each photosensor is a device which transduces optical energy directed at the surface of this sensor into an electrically registered signal. Photosensors are selected to be responsive to optical emission wavelengths of the photoluminescent assay labels. These photosensors may be selected from, for example: photodiodes, phototransistors, photoresistors, charge coupled devices, or photon multiplier tubes.

In an embodiment of the present invention, a collection lens is located within the collection light path and collects light emitted from an excitation area, that area of the immunoassay surface illuminated by the excitation optical assembly, and directs this light towards a corresponding photosensor. In a specific embodiment of the present invention, the collection lens directs light emitted from the full excitation area to the central portion of a corresponding photosensor. In this case, selection of the size of the excitation area and the integration of the optical signal over the full excitation area is carried out to afford resilience to local inhomogeneity in the assay materials. Also, as light is directed towards the centre of the sensor, the system may withstand some misalignment of the optics before light is transferred to an area outside the active area of the photosensor. A collection lens may be formed of one of a variety of transparent materials; including glass, fused silica or organic polymers (e.g., polymethylmethacrylate, polycarbonate, polytetrafluoroethylene, polystyrene or cyclic olefin co-polymer). Generally a collection lens is of a light converging form, with the design of the lens being one of, for example: convex, bi-convex, spherical, plano-convex, positive meniscus or aspheric. Lens parameters include focal length, numerical aperture, material and coatings. These are selected to optimise the optical design and conform to the wavelengths of collection.

In particular embodiments of the present invention, collection optics also comprise one or more optical filters [308]. Such a filter is located within the optical collection path. The optical collection filter shapes the spectral profile of collected light prior to detection by the photosensor. This filter acts to ensure that residual excitation light is not transmitted to the photosensor. An optical collection filter may, for example, be of band-pass or long-pass variety, and may operate by interference or absorptive mechanisms. The filter specification is selected to have a stop-band including the spectral bandwidth of the excitation light source, following optical filtration by any excitation filter, and a pass-band including some portion of the emission wavelengths of the photoluminescent labels. In an embodiment, a long pass absorptive optical collection filter is selected. In the particular case of an interference-type collection filter, an additional collection lens may be present in the reader device. In this case, the first collection lens may be located within the collection light path and collects light emitted from an excitation area, that area of the immunoassay surface illuminated by the excitation optical assembly, and acts to collimate or partially collimate this light. The interference-type collection filter can be placed between this first collection lens, and the second collection lens. The second collection lens can direct the filtered light towards a corresponding photosensor. In a particular embodiment of the present invention, there may be an angular offset between the plane of optical collection paths of the collection optics, and the plane of optical excitation paths of the excitation optics. The angular position of these planes and their specific offset can be selected in order to inhibit direct reflection of excitation light into the detector assembly. In an embodiment, as shown in FIG. 15(a), the optical excitation plane is normal to the cartridge surface, while detection is offset by 35 degrees.

In particular embodiments of the present invention, the reader system is capable of selecting one of multiple optical wavelength bands for optical excitation of the sample, corresponding to the excitation wavelengths of one of multiple photoluminescent labels associated with the mobilizable or control reagents of immunoassays. Likewise, the reader system is capable of selecting one of a variety of various optical wavelength bands for detection of the optical signals corresponding to the emission wavelengths of one of multiple photoluminescent labels associated with the mobilizable or control reagents of immunoassays. In this regard, the reader may incorporate multiple excitation sources; consisting of multiple banks of LEDs or other excitation light sources, each bank emitting optical radiation at a particular central wavelength. The specific bank of excitation sources used for optical excitation of the sample during a scan is selected with regard to the excitation maxima of the photoluminescent labels. Each bank of excitation light sources may have an associated optical excitation filter and aperture plate. The banks of excitation light sources may be placed at 90 degrees to one another, at similar distances from the sample plane. Light emitted from one bank of excitation light sources may be normal to the sample plane.

Figure 4:
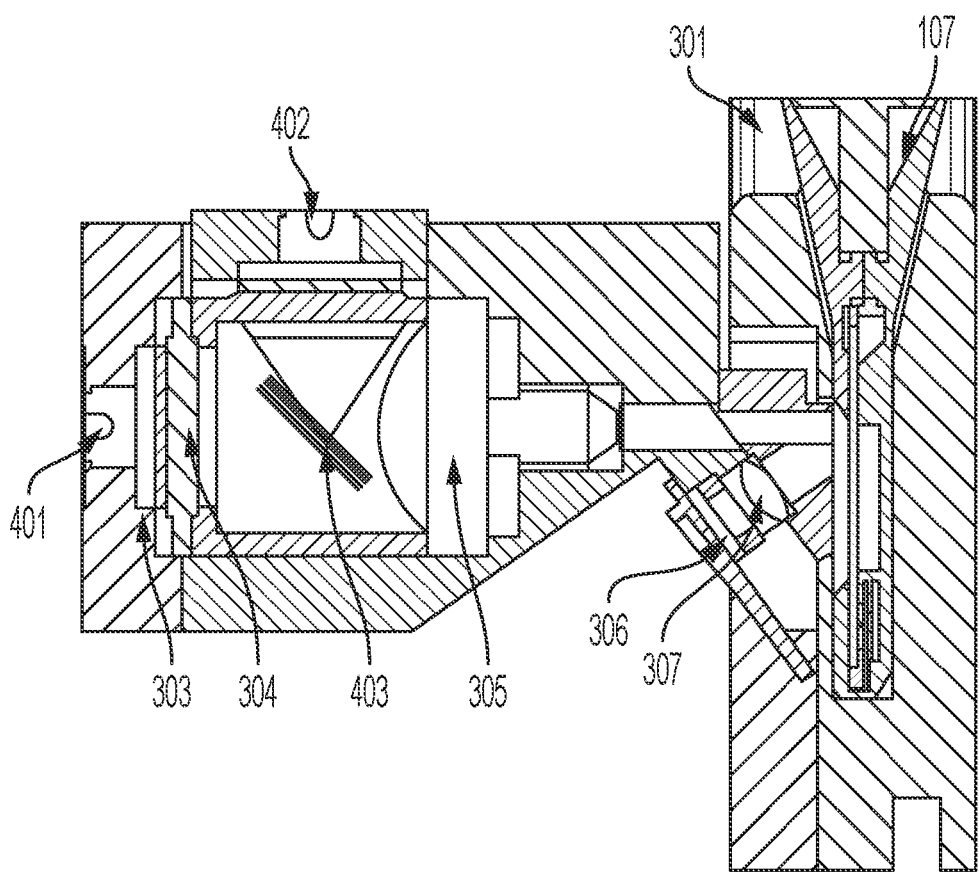
FIG. 4 shows a reader optics diagram for a multiple wavelength system.

In an embodiment of the reader system, as shown in FIG. 4, two banks of LEDs [401], [402] are used with directions of emission normal to and parallel to the sample surface. A half-reflective mirror [403] is placed in the excitation light paths at 45 degrees from each of the LED bank's nominal light paths, such that some portion of light emitted from each bank is directed to produce excitation areas upon the immunoassay surface at similar positions and dimensions. The reader's nominal excitation wavelength is then selected by activating only the LED bank of this wavelength.

In an alternative embodiment of the reader system, two banks of LEDs are used, with directions of emission normal to and parallel to the sample surface. A mechanically actuated mirror is placed such that it may be moved into an "engaged" position within the excitation light paths, at 45 degrees from each of the LED bank's nominal light paths. In this case, light originating from the LED bank with emission normal to the sample surface has its emission blocked, while that with emission parallel to the assay surface has its light reflected to form excitation areas on the assay surface. Thus, actuation to the "engaged" position ensures excitation of the sample using a first wavelength. In a "non-engaged" position, the mirror is in neither of the optical light paths. In this case, light originating from the LED bank with emission normal to the sample surface forms excitation areas on the assay surface, while light originating from the LED bank with emission parallel to the assay surface does not reach the assay surface. Thus, actuation to the "non-engaged" position ensures excitation of the sample using the second wavelength.

In particular embodiments of the present invention, the reader may select between specific wavelength ranges of sensitivity in detection. In this regard, a mechanically actuated selection of optical filters is present within the collection assembly, such as a motor turned filter wheel. Selection of a particular filter ensures that this filter lies within the collection optical path for a particular scan. In this regard, collected light with energies corresponding to the pass-range of this filter is transmitted to the optical detector, determining the optical wavelength response of the reader. The particular filter selected in an assay scan is selected to ensure transmission of some portion of the light emitted by the photoluminescent labels associated with the mobilizable or control reagents of immunoassays, and exclusion of stray excitation light. Alternatively, multiple light collection assemblies may be present within the reader system with various spectral sensitivities. For example, the reader system may incorporate a second set of lens, filer and detector elements in a mirrored layout to the previously specified assemblies. This may be located at an angle above the plane of cartridge excitation. In this case the collection filters may be each long-pass or bandpass in character, and may be tuned to pass substantially different wavelengths bands of light. By simultaneous, or temporally separated monitoring of photodetector signals or each detector assembly emission from multiple spectrally separated photoluminescent labels may be distinguished within a single scan. In this regard, the reader instrument is able to address and separately register multiple different sets of overlapping emissive features within a single channel.

In an embodiment of the present invention, the reader system incorporates one or more digital processors and electronics for the actuation and control of readings. Generally, these control the operation of motors, optical electronic components, display components, and scan processing. Digital processors also interpret data entry and communications protocols. Additionally, the digital processors control any internal digital memory; enabling the writing, reading, search and transfer of data. The digital processors carry out scan processing and interpretation algorithms, and controls the various electronic components of the reader devices.

In some embodiments, a reader system includes non-volatile or volatile digital memory for the storing of data. Generally, such data may include collected scan data, and corresponding patient details and assay results; user details and passwords; events and error logs; calibration parameters; reader settings; user interface screens; interface and communications parameters; and reader operation programs. This memory may consist of one of, or multiple instances of, for example, internal flash memory, magnetic hard-drives, and SD-card components.

In some embodiments, a reader system includes one or more communications ports. Components and protocols are incorporated for wired connectivity, such as universal serial bus (USB), Ethernet (IEEE 802.3), and serial recommended standard 232 (RS-232). These facilitate communication to devices external to the reader, such as personal computers or mobile devices. These may also enable control and powering of external devices, such as barcode readers or printers. These may also facilitate connections to hospital or laboratory information management systems. In an embodiment, this connectivity enables remote diagnostics, firmware or software updates and data transfer, and control of an external barcode reader device.

In some embodiments, a reader system includes components and protocols for external wireless access, such as by Wi-Fi (IEEE 802.11), ANT or Bluetooth. These facilitate communication to, or control of, devices external to the reader. These may also facilitate connections to hospital or laboratory information management systems. In an embodiment, this connectivity enables remote diagnostics, firmware or software updates and data transfer.

In some embodiments, a reader system includes a printer for the printout of hardcopies of scan results and associated audit data following the reading of an assay, or from stored memory. Additional printable data may include: user lists, reader settings, events or error logs, installed calibrations, quality control results, etc. This printer may be of a type including: thermal, ink-jet, laser, or dot-matrix. In an embodiment, this reader is within the reader casing and is of thermal type.

In some embodiments, a reader system is portable, being intended for bench- or table-top point-of-care use. In an embodiment of the present invention, the reader includes an internal rechargeable battery, which may power the reader in situations where the system is not connected to mains power supplies. This battery is rechargeable, and charges while the reader is connected to a mains power supply. Electronics and the digital processor may monitor battery charge, reporting this to the user, and regulating such details as: charge speed, battery temperature, and minimum charge levels before the unit is automatically shut down. In certain embodiments of the reader system, batteries may be held in a removable battery pack, or be insertable into a dedicated battery compartment by the user. In certain embodiments, a reader system incorporates a speaker for transmission of auditory alarms, or auditory feedback or user actions. In certain embodiments, the reader comprises an internal clock. This clock is generally powered by a separate, long life battery component.

In an embodiment of the present invention, a Secure Digital (SD) card component holds assay specific calibration data relating to an assay cartridge batch. The SD card may be introduced into the reader system, and the assay specific calibration data copied to internal reader memory. In an embodiment of the present invention, the SD card is a secure write-once, read many times form. This card may be encoded with identification data corresponding to unique characteristics of the particular card, enabling security of written data and recognition of the correct card type prior to transfer of information.

In an embodiment of the current invention, an SD card may hold firmware or software updates for the reader device. Alternatively, a standard SD card may be inserted into the SD card slot, and the user may transfer saved data (such as scans, results, settings, calibrations or quality control data) from the internal device to the SD card for back up or subsequent transport.

In an embodiment of the present invention, the excitation source activation and emission timings and photosensor read timings are tuned in accordance with the positions and numbers of assay channels within the immunoassay cartridge. These parameters may be stored in the batch calibration file, and the excitation and read logic of the reader system is modified with regard to the cartridge structure. For example, in a reader system with six channels, the system is presented with a three channel immunoassay cartridge. The reader system is informed of the positions of the present assay channels, and acts to only excite and read from these channels, modifying the relevant timings accordingly.

In an embodiment of the present invention, the excitation source emission timings and photosensor read timings are tuned such that only one test is being excited at a specific time, ensuring that optical crosstalk between channels is minimised. Alternatively, multiple channels may be illuminated and read simultaneously. However, these channels may be spatially separated in order to ensuring that optical crosstalk between channels is minimised.

In an embodiment of the present invention, electronic frequency filtering is applied to the photosensor signal. The pass-band of this electronic filter is tuned to the frequency of the excitation source duty cycle, and serves to amplify the detected photoluminescence while attenuating noise signals. Such noise may be associated with constant (low frequency) light leakage into the system, or high frequency electronic noise. Such a filter may be comprised of multiple high-pass and low-pass electronic filters placed in series.

In an embodiment of the present invention, a reader system records a dark count, corresponding to detected signal from each channel without activation of the corresponding light source for an equivalent time to the defined excitation source emission time and at a time close to each excitation duty cycle. In this case, the photosensor signals may be corrected by subtraction of this dark count from that acquired during activation of the corresponding light source. This enables compensation for light leakage into the device, interference from light generation within the device, or thermal or electronic noise.

In an embodiment of this invention, time resolved detection of photoluminescence may be employed in the reader system. In this regard, an excitation source may be activated briefly, and corresponding photoluminescence recording initiated some time (generally at least tens to hundreds of nanoseconds) after the light source has been deactivated. In this manner, photoluminescence from long emissive lifetime (for example, lanthanide labels with emissive lifetimes of multiple microseconds) photoluminescent labels may be discriminated from shorter lifetime background fluorescence (generally termed in nanoseconds).

In an embodiment of this invention, the light source optical emission intensity is controlled and stabilised through the cartridge scan. In this case, the excitation optics incorporates a dedicated excitation source monitoring photosensor. The light source emission intensity is thereby monitored by analysis of the monitoring photosensor electronic signal Feedback of this monitoring signal to the excitation source may ensure that the that the emission of the excitation source remains constant across all scans. Feedback stabilization may be carried out throughout a scan, across each duty cycle of each light source's emission. Alternatively, feedback stabilization may be independently carried out for each light source prior to the commencement of each cartridge scan. In an embodiment of this invention, the reader incorporates a proportional-integral-derivative control algorithm to optimally stabilise light source emission at a desired intensity by analysis of the monitoring photosensor signal.

In some embodiments, a reader system uses an algorithm for the detection of optical emission peaks from each optical scan. Algorithm parameters may include such details as expected numbers of peaks, expected peak scan positions, expected widths of peaks, expected ranges of peak heights. Peak detection algorithms may include background subtraction; compensating for background fluorescence derived from the assay materials, stray background light, unbound labelled assay materials or other sources. This may be realised by subtracting the minima of a scan, or estimation and subsequent subtraction of background fluorescence at the point of the peak maximum. In an embodiment, such an estimation is carried out by registering fluorescence levels at particular scan positions at a defined distance to either side of the peak position, then determining a linear fit to the background versus scan position, and finally estimating the level of background fluorescence at a scan position at a position corresponding to the peak maximum.

In particular embodiments of the present invention, sets of quality controls are actualised in software to ensure that the assay progressed in a defined manner. These may include: quality control checks of scan data, including a check of control line development, a check of channel clearance, and checks as to the size and position of peaks. Additionally, controls may verify the time of test as being within the expiry data of a particular assay. In particular, the level of detected luminescence is characterised at a particular scan position, defined in calibration parameters for the assay in question, at which no capture or control zones are present, and which generally corresponds to background fluorescence. If the magnitude of this photoluminescence is found to be above a certain level defined in calibration parameters for the assay in question, the unbound luminescent materials is not taken to have achieved full clearance, and the particular assay is termed a "Missrun". Control zone peaks are further analysed: if these are not found, or are of insufficient magnitude, the assay is likewise is considered to have not fully developed, and is likewise termed a "Missrun".

In an embodiment of the present invention, the reader includes a calibration algorithm for the qualification or quantification of analyte presence within an immunoassay fluid sample. These algorithms take as input the following: calibration parameters specific to the assay batch and peak heights as determined by a peak detection algorithm for each of the capture and control zones. For each analyte, the algorithm processes the corresponding capture zone peak height, according to the calibration parameters. Alternative algorithms may alternatively normalize the capture zone peak height by the control zone peak height, compensating for flow related or assay component related variability. Generally for qualitative tests, the algorithm compares the peak height versus a threshold value, and reports a positive or negative result. Alternatively for quantitative tests, the algorithm characterises the concentration of an analyte within the test sample, according to assay specific calibration parameters. In this case, the algorithm may report that the concentration is greater or less than particular limits of quantization, respectively. Finally, for semi-quantitative tests, the algorithm characterises the concentration of an analyte within the test sample to be within specific ranges, according to assay specific calibration parameters. It should be understood that a multiplex assay panel may consist of a selection of qualitative, quantitative and semi-quantitative assays, all within a single cartridge, being read and interpreted simultaneously.

In the case where the assay batch includes parallel tests for a particular analyte with similar sensitivities, an alternative calibration algorithm may take as input the following: calibration parameters specific to the assay batch and peak heights as determined by a peak detection algorithm for each of the capture and control zones for each of the parallel tests. For each analyte, the algorithm processes the corresponding capture zone peak heights, according to the calibration parameters. Estimation error in the quantitative or quantitative estimate of analyte presence may be minimised by averaging multiple results, or by discarding results with outlying values or corresponding peak heights.

In the case where the assay batch includes parallel tests for a particular analyte with varying sensitivities and corresponding linear ranges, an alternative calibration algorithm may take as input the following: calibration parameters specific to the assay batch and peak heights as determined by a peak detection algorithm for each of the capture and control zones for each of the parallel tests. For each analyte, the algorithm processes the corresponding capture zone peak heights, according to the calibration parameters. The algorithm then selects a result predicted by one test in which the quantitative measurement is within the linear range of the test. Additionally, where the measurement is within the linear range of multiple tests, the algorithm may report the result as the weighted average of the analyte concentrations estimated from each such test.

Finally, in the case where the assay batch includes various tests related to single or multiple clinical decisions, a secondary algorithm may take as input the quantitative or qualitative estimates from each individual test as provided by the calibration algorithm. This secondary algorithm processes the various calibration results and reports a single diagnostic result or multiple diagnostic result.

In an embodiment of the present invention, a physically separate quality control component, of external dimensions similar to that of the assay cartridge is incorporated. This component incorporates materials exhibiting specific, characterised efficiencies of photoluminescence upon optical excitation at a wavelength corresponding to the reader excitation source. In an alternative embodiment of the current invention, the quality control component may be disposed on each assay cartridge, at a position separate from the assays. In another embodiment of the current invention, the quality control component may be integrated within the reader system itself. In particular embodiments of the current invention, the quality control component may be integrated within the reader's cartridge holster, being automatically actuated to and from the optical plane upon removal and insertion of the test cartridge, respectively.

In embodiments of the present invention, the quality control component's photoluminescent areas are defined using masked photoluminescent materials, coated non-fluorescent materials or multilayer etched materials. Photoluminescent materials may consist of plastics impregnated with fluorescent dyes, nanocrystals or quantum dots.

In embodiments of the present invention, the quality control component's photoluminescent areas may be localised at the optical plane within the reader. Photoluminescent areas are patterned in a defined manner, such that optical misalignments will lead to predictable changes in scan responses.

In a first embodiment of the present invention, a processing algorithm for the analysis of quality control component scans is incorporated. This algorithm will compare the expected response from fluorescent areas with those of received responses, and validate the reader for the analysis of assays. In a second embodiment of the present invention, the algorithm will compare the expected response from fluorescent areas with those of received responses, and compensate for changes in system response by the modification of internal calibration factors. In a third embodiment of the present invention, the algorithm compares the reader response with the expected response from the patterned fluorescent component. This algorithm then calculates the type and degree of optical misalignment, such as: the direction and degree of lateral misalignment, degree of focus or defocus, or optical system tilt. In this case, the reader may incorporate motor driven alignment of the optical stage. Reader algorithms analyse the quality control component scan, and automatically adjust the position of the optical stage for optimal system alignment.

In an embodiment of this invention, the reader incorporates a processing algorithm for the verification of immunoassay batch response. This algorithm analyses the response of one or more immunoassay cartridges of the specified batch, run with control liquids of specified concentrations. The algorithm compares expected responses with those found from these cartridges, and verifies the immunoassay batch as operating to a given specification. Further, this algorithm also may conduct the optimisation and correction of immunoassay batch specific calibration parameters, as stored within reader memory, to compensate for time-related changes in immunoassay photoluminescence response. In this case, following the analysis of one or more immunoassay cartridges of the specified batch, run with control liquids of specified concentrations, internal calibration parameters are then updated to provide a best-fit result to control responses.

Embodiments of the present invention include procedures and methods for updating reader software and firmware. In certain embodiments, an update may be initiated by the user selecting particular menu options of the reader's user interface. The reader system may receive data corresponding to the compiled firmware or software code from a variety of sources, including but not limited to: an SD card inserted into the SD card port, a USB flash drive inserted into a USB port, an external connected personal computer, or a wireless connection. In certain embodiments of the reader system, firmware or software updates have "roll-back" functionality, affording a reset to factory settings or a previous firmware or software version if the update does not proceed correctly.

Test Scan Procedure

Figure 5:
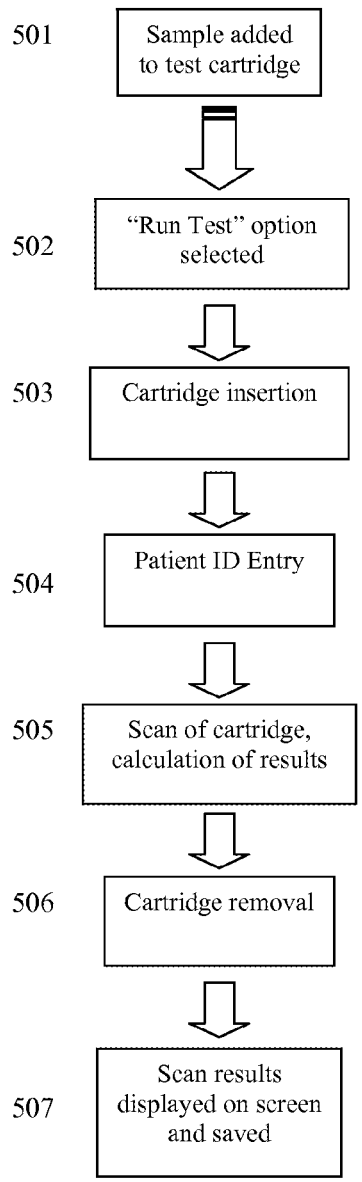
FIG. 5 shows a reader use procedure block diagram for a test scan.

In an exemplary embodiment of the present invention, an operation procedure for the conducting of test scans may be summarised as follows (shown in FIG. 5): The user adds a fluid sample to the assay cartridge, and the assay cartridge is left for sufficient time for the assay to develop [501]. Next, the user selects the "run test" option of the reader's user-interface [502]. The reader system lifts the cartridge holster to a cartridge access position, opening the reader lid [201], and prompts the user to insert the assay cartridge [503]. Upon insertion of the cartridge, the holster is brought to a "home" position, and the user is prompted to enter a patient identification (via the integrated text entry device, or external barcode reader) [504]. The system carried out a scan of the assay panel, and calculates assay results [505]. The cartridge holster is brought back to the access position, opening the reader lid, and the user is prompted to remove the cartridge [506]. Finally, results are displayed on the reader screen, and are automatically saved [507].

Liquid Calibrator Scan Procedure

Figure 7:
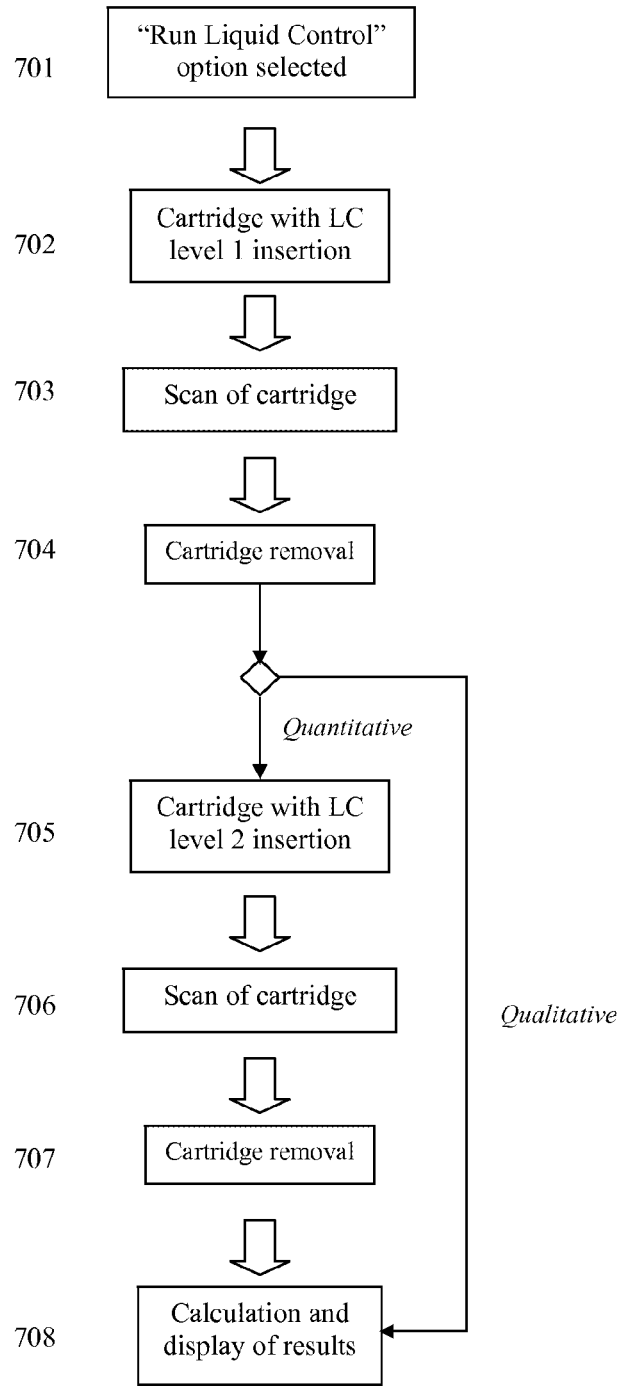
FIG. 7 shows a reader use procedure block diagram for liquid controls scans.

In an exemplary embodiment of the present invention, the operation procedure for the conducting of liquid calibrator scans to account for assay changes over time may be summarised as follows (shown in FIG. 7): The user adds a "level one" liquid control sample (with a characterised concentration of each analyte) to a standard assay cartridge of the batch to be corrected, and the assay cartridge is left for sufficient time for the assay to develop. Next, the user selects the "run liquid control" option of the reader's user-interface [701]. The reader system brings the cartridge holster to an access position, opening the reader lid, and prompts the user to insert the assay cartridge [702]. The system carried out a scan of the cartridge assay panel, and processes the raw data [703]. The cartridge holster is brought back to the access position, opening the reader lid, and the user is prompted to remove the cartridge [704].

If the assay batch corresponds to a quantitative assay panel, the user is then prompted to add a "level two" liquid control sample (with a second characterised concentration of each analyte) to a second standard assay cartridge of this batch. The user leaves the assay cartridge for sufficient time for the assay panel to develop, before inserting the assay cartridge into the reader system [705]. The system carried out a scan of the assay panel, and processes the raw data [706]. The cartridge holster is brought back to the access position, opening the reader lid, and the user is prompted to remove the cartridge [707].

In the case of either a qualitative or quantitative assay batch, results are then calculated from the processed raw data, displayed on the reader screen, and automatically saved [708].

Scan Processing

In embodiments of the present invention, raw scan response data acquired during either test scans or liquid control scans are processed prior to estimation of analyte presence or concentration. This processing calibrates the data to account for reader response, which may be somewhat different between reader channels, or between reader models. Following this, peaks are detected in the reader calibrated data, according to peak detection parameters stored within corresponding batch calibration files. Finally, the data is checked for read or assay run errors.

Figure 8:
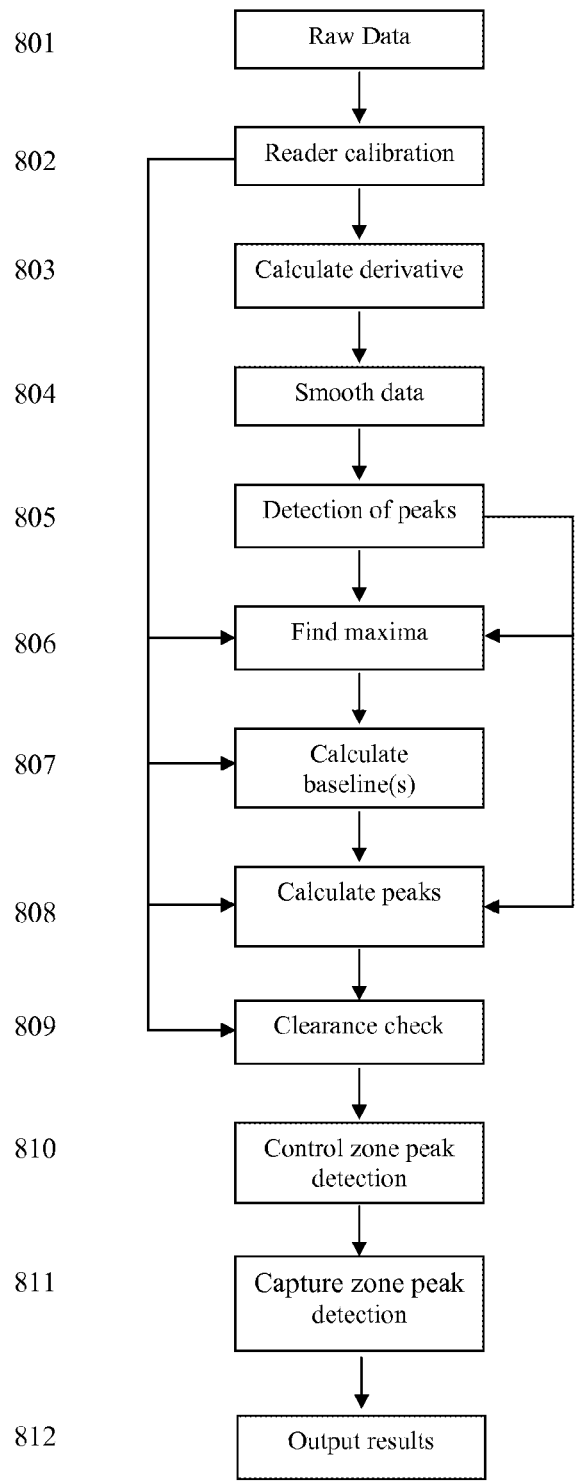
FIG. 8 shows a scan processing algorithm block diagram.

In an exemplary embodiment of the present invention, the algorithm utilised for the processing of raw scan data, following a test scan or liquid calibrator scan, but prior to assay calibration or calculation of liquid calibrator results may be summarised as follows (as shown in FIG. 8): Initially the raw data, corresponding to optical energy collected by a reader photosensor at points across the scan length [801], is scaled by an internal reader calibration function [802]. This function is generally of the form of a linear equation, and normalises each point of the data set accounts for inter- or intra-reader variability, and is stored in non-volatile memory within the reader system itself.

Figure 16:
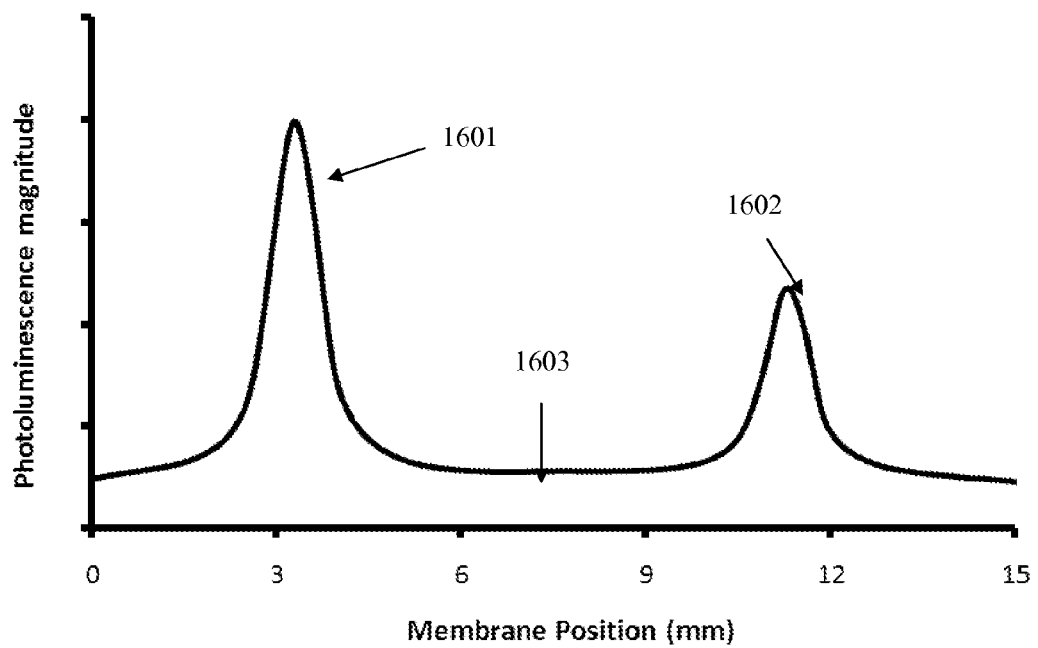
FIG. 16 shows an example optical scan taken by an reader system.

Next, analysis of peaks within the reader calibrated scan data is carried out. A scan of a single cartridge channel may incorporate a control capture zone peak and any number of mobilizable reagent capture peaks. Generally, each mobilizable reagent capture peak is associated with a separate assayed analyte within the fluid sample. An example calibrated scan is shown in FIG. 16 for a single channel. This figure shows a peak corresponding to the control reagent capture zone [1601], and a peak corresponding to photoluminescence from the mobilizable reagent capture zone [1602]. Generally, the reader system incorporates an algorithm for the detection of optical emission peaks, corresponding to labelled mobilizable or control reagent capture zones from each optical scan. Algorithm parameters may include such details as expected numbers of peaks, expected scan positions of peaks, expected widths of peaks, and expected ranges of peak heights. Peak detection algorithms may include background subtraction; compensating for background fluorescence derived from the assay materials, stray background light, unbound labelled assay materials or other sources [1603]. This may be realised by subtracting the minima of a scan, or estimation of background luminescence at the scan position of the photoluminescence peak maximum. In an embodiment, such estimation is carried out by registering luminescence levels at particular scan positions at a defined distance to either side of the peak position, determining a linear fit to the background versus scan position, and then estimating the level of background fluorescence at a scan position corresponding to the peak maximum.

In a particular embodiment of the current invention, an algorithm is incorporated which searches for specific peaks within the optical scan data. The block-diagram operation of this algorithm is shown in FIG. 8. Parameters for the peak recognition are provided in the lot calibration file, which is generally stored in reader memory. Initially, the algorithm processes the reader calibrated data [802] by determining the differential of this data [803]. Next, the differential is smoothed using a Savitsky Golay smoothing filter [804]. Following this, each peak is detected by searching for corresponding rising edges, falling edges and zero-crossing points within the smoothed differential data; with search parameters in accordance with those stored within the batch calibration file [805]. The algorithm analysis derives the positions of the scan maxima for each peak. These positions may be further refined by interpolation. Subsequently, a maximum response value is searched for in the original scan response data [806]. This search is carried out between scan positions corresponding to the smoothed differential's rising and falling edges, respectively.

A background luminescence baseline is estimated by fitting a linear function between two points [807]. These points correspond to average values of luminescence about two positions at set distances either side of the corresponding peak maximum. Finally, the background corrected peak height is estimated by subtracting the value of this linear function at the position of the scan maximum from the peak maximum itself [808]. This algorithm is carried out for each peak in the scan data.

In particular embodiments of the present invention, prior to running a scan, the reader software initially verifies the date of testing as being prior to the expiry date of a particular assay, and that the test date and time being within a set period of time since the reader optical quality control checks, or liquid control verification or calibration corrections of the cartridge batch in question. In addition, sets of quality controls may be actualised in software to verify that the assay ran in a defined manner. These may include: quality control check of scan data, including a check of control line development, a check of channel clearance, and checks as to the size and position of peaks. In particular, the level of detected luminescence is characterised at a particular scan position, defined in calibration parameters for the assay in question, at which no capture or control zones are present, and which generally corresponds to background fluorescence. If this luminescence is found to be above a certain level defined in calibration parameters for the assay in question, the unbound luminescent materials is not taken to have achieved full clearance, and the particular assay is termed a "Missrun" [809]. Control zone peaks are further analysed: if these are not found, or are of insufficient magnitude, the assay is likewise is considered to have not fully developed, and is likewise termed a "Missrun" [810]. In either case, no estimate is made of analyte concentration or presence. Following this, the algorithm verifies that a capture zone peak was detected. If this is not the case, the algorithm interprets the magnitude of the capture zone peak to be negligible and a capture zone peak height value of "0" is utilised for assay calculations [811]. Finally, the results are output for analysis by the relevant test scan calibration algorithm, or liquid control algorithm [812].

Algorithm for Calibration of Test Scans

In an embodiment of the present invention, the reader includes a calibration algorithm for the qualification or quantification of luminescence from active areas of an assay scan. This algorithm takes as input the following: calibration parameters specific to the assay batch and peak heights as determined by a peak detection algorithm for each of the capture and control zones. For each analyte, the algorithm processes the corresponding capture zone peak height, according to the calibration parameters. Generally for qualitative tests, the algorithm compares a scaled peak height versus a threshold value, and reports a "positive" or "negative" test result. Alternatively for quantitative tests, the algorithm characterises the concentration of an analyte within the test sample, according to assay specific calibration parameters. In this case, the algorithm may report that the concentration is less than a particular limits of detection, or greater or less than particular limits of quantization, respectively. Finally for semi-quantitative tests, the algorithm characterises the concentration of an analyte within the test sample to be within specific ranges, according to assay specific calibration parameters. It should be understood that a multiplex assay panel may consist of a selection of qualitative, quantitative and semi-quantitative assays, all within a single cartridge, being read and interpreted simultaneously.

Figure 9:
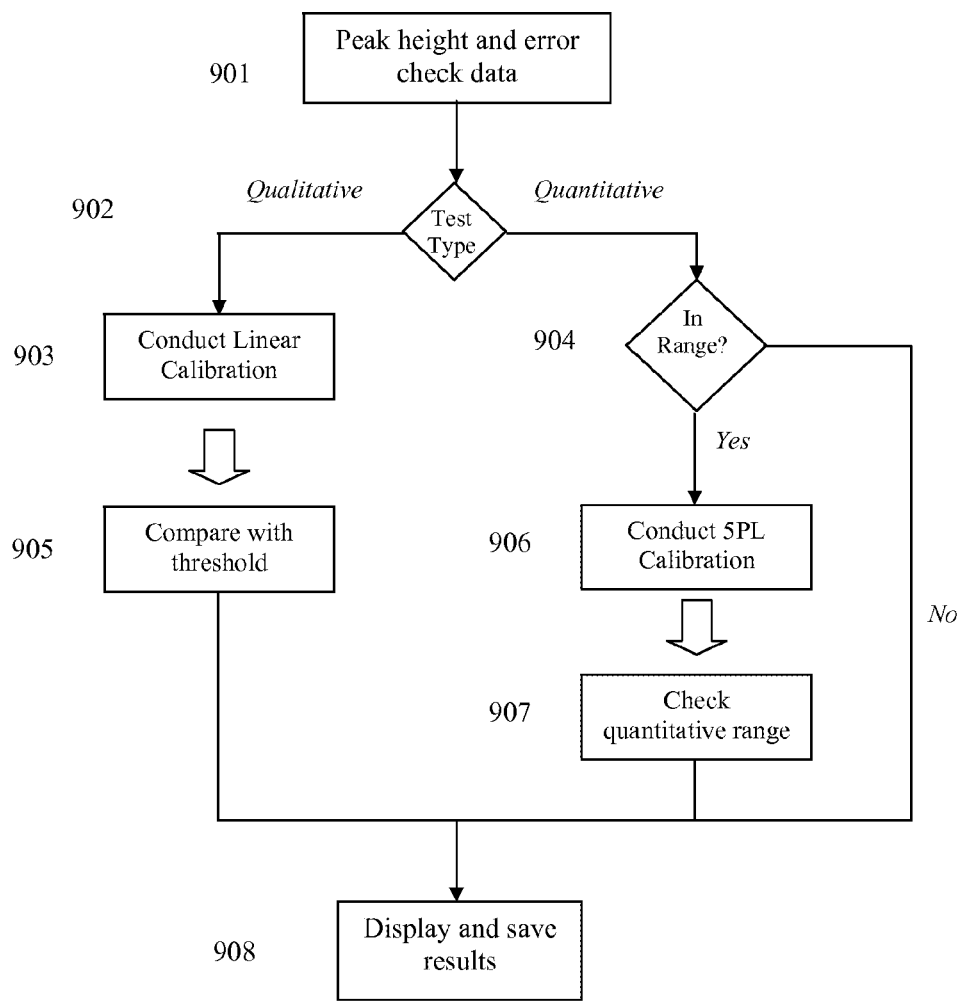
FIG. 9 shows a test scan calibration algorithm block diagram.

In an exemplary embodiment of the present invention, the test scan calibration algorithm may be summarised by FIG. 9. Taking as inputs the peak height and error check data [901], and assay calibration parameters as given in the corresponding cartridge batch calibration file, the algorithm determines the nature of the assay—either as a quantitative or qualitative assay [902]. In the case of a qualitative assay, the algorithm may use a linear equation for calibrating the capture zone peak height to account for variations in the assay batch response over time [903]. The coefficients of this calibration function are stored in the corresponding cartridge batch calibration file. The scaled response is subsequently compared with the response threshold value [905], which is also stored in the corresponding cartridge batch calibration file. In the case of a competitive assay, if the response is below this threshold, the assay is reported as positive for the analyte in question. Otherwise, the assay is reported as negative. In the case of a sandwich assay, if the response is below this threshold, the assay is reported as negative for the analyte in question. Otherwise, the assay is reported as positive.

In the case of a quantitative assay, the algorithm may use a 5-parameter log-logistic equation to estimate the analyte concentration from the capture zone peak height.

Initially, the capture zone peak height is analysed to ensure it is within the range of the calibration 5-parameter log-logistic curve equation [904]. If the capture zone peak height is within the range of the calibration equation, calibration is carried out with regard to the 5-parameter log-logistic equation, and the estimated analyte concentration determined [906]. Otherwise, the concentration may be reported as beyond the respective limit of quantization.

The estimated analyte concentration is next compared against the lower concentration limit of quantization, and the upper concentration limit of quantization, as given in the cartridge batch calibration file for the assay in question [907]. If the estimated concentration is outside one of these bounds, reporting is carried out as: If the calculated concentration is below a stipulated lower limit of quantization, the result is given as below this limit, rather than the estimated concentration. Conversely, if the calculated concentration is above a stipulated upper limit of quantization, the result is given as above this limit, rather than the estimated concentration.

Finally, the respective results, specifically run errors and presence or concentration estimation results are reported to the user, and these results saved [908].

Liquid Control Algorithms

In an embodiment of the present invention, the reader includes a processing algorithm for the updating of assay specific calibration parameters to compensate for assay-related changes in mobilizable reagent capture zone luminescence response. This algorithm analyses the response of one or more assay cartridges of the specified batch run with control liquids of specified analyte concentrations. Internal calibration parameters are then updated to provide a best-fit result to control responses.

In an embodiment of the present invention, liquid calibrators are used to account for minor assay and reader changes over time. These are generally run and analysed by the corresponding liquid control algorithm on a monthly basis for each batch of assays. However, the required frequency of this correction may be set by the administrator level user.

In an exemplary embodiment of the present invention, one stable control liquid is run to recalibrate a single assay batch for qualitative assays. This control liquid contains defined concentrations of the analytes of interest. Generally, these concentrations are selected to correspond to the concentration thresholds for each of the analytes. A specific quantity of each control liquid is run in an individual, standard cartridge of that batch. Conversely for quantitative assays, two stable control liquids are run to recalibrate a single assay batch. Each of the two liquid controls contains defined concentrations of the analytes of interest. Generally, the two concentrations of each analyte are selected to correspond with defined low and high concentrations, respectively, with mobilizable reagent capture zone luminescence responses within the linear range of the 5-parameter log-logistic curve equation. A specific quantity of each control liquid is run in an individual, standard cartridge of that batch.

Figure 11:
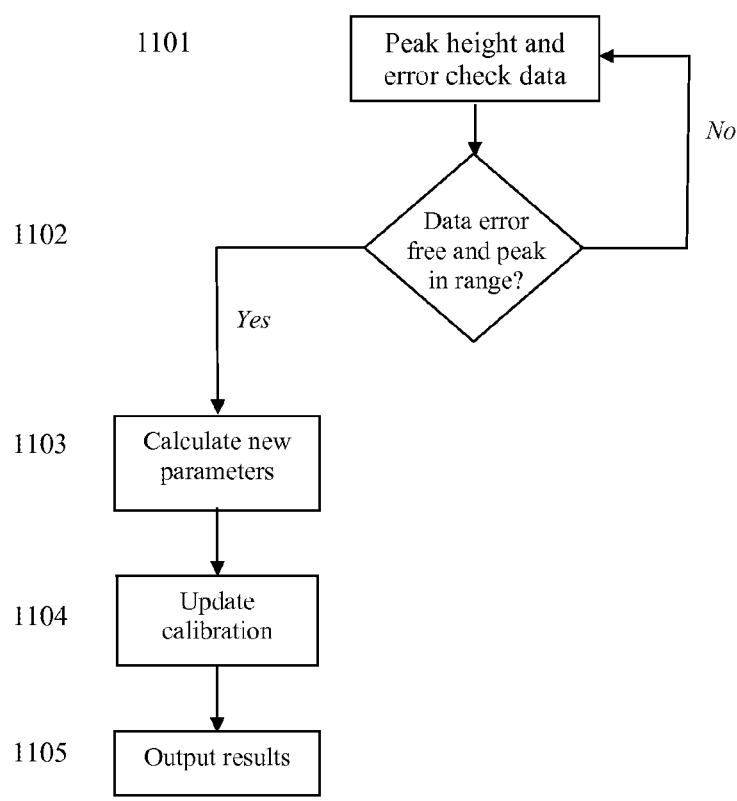
FIG. 11 shows a liquid controls calibration adjustment algorithm block diagram for a qualitative tests.

An example of a liquid control calibration adjustment algorithm for a qualitative test is shown in FIG. 11. Upon acquisition and processing of scan data from the "level one" liquid control [1101], this data is verified to ensure that no miss-run has occurred, and that the capture zone peak of each assay analyte is within an expected range [1102]. If either of these checks is failed, the user is prompted to repeat the liquid control calibration adjustment.

If these checks are passed for all assays, a new linear equation for calibrating the capture zone peak height to account for variations in the assay batch response over time is calculated.

Finally, the calibration file is updated with the new value of the linear equation, and the result of the liquid calibration displayed for the user.

Figure 12:
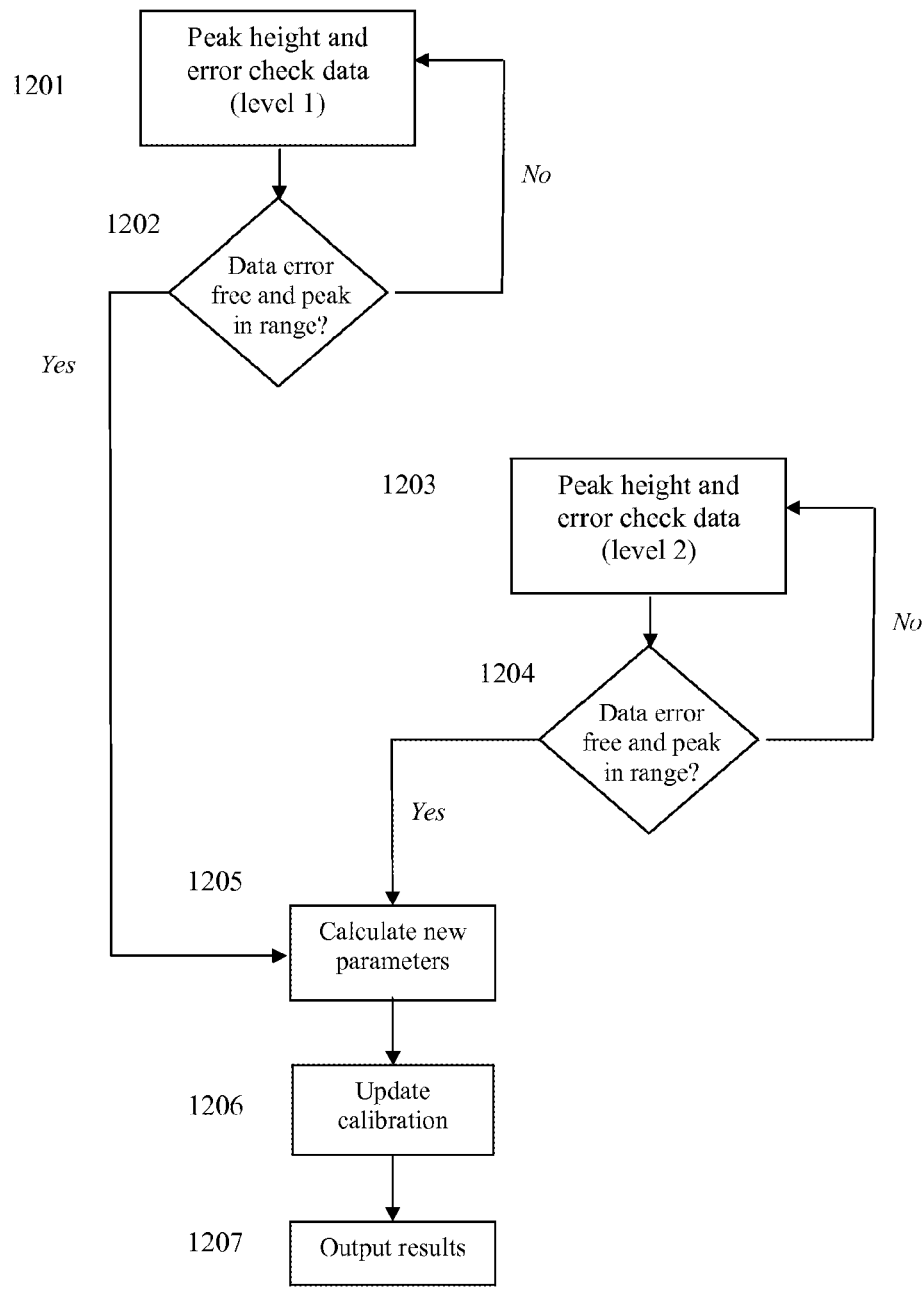
FIG. 12 shows a liquid controls calibration adjustment algorithm block diagram for a quantitative test.
Figure 14:
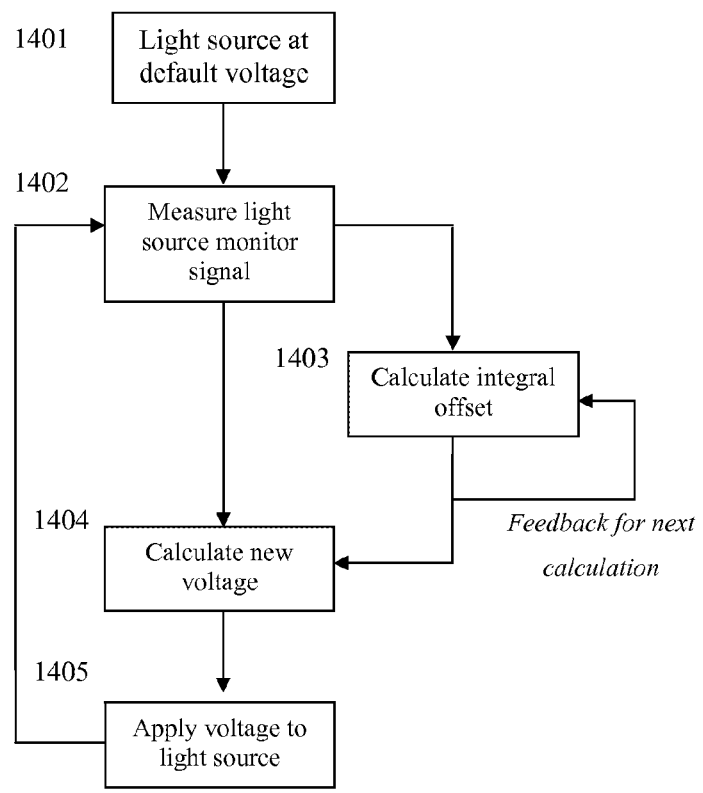
FIG. 14 shows a schematic of sample light source emission power feedback algorithm.

An example of a liquid control calibration adjustment algorithm for a quantitative test is shown in FIG. 12. Upon acquisition and processing of scan data from the "level one" (e.g., low concentration levels) liquid control [1201], this data is verified to ensure that no missrun has occurred. Next, the estimated concentration of analyte is calculated; in an identical manner to that of a standard test scan. For this purpose, the original values for 5-parameter log logistic equation are used, as given in the batch calibration file. This equation is prior to corrections carried out in previous liquid controls, and this step verifies the assay is still operating in a similar manner to that of the freshly manufactured batch. This estimated concentration is then validated, verifying this is within a set range, of the actual concentration of the "level one" liquid control (also given in the batch calibration file). If no error has occurred, and the estimated concentration is within the expected range, the raw and processed peak data is saved, and the "level two" liquid control calibrator is called for. Alternatively, the user is prompted to repeat the "level one" liquid control calibrator [1202].

Upon acquisition and processing of scan data from the "level two" (e.g., high concentration levels) liquid control [1203], this data is verified to ensure that no missrun has occurred. Next, the estimated concentration of analyte is calculated; in an identical manner to that of a standard test scan. For this purpose, the original values for 5-parameter log logistic equation are used, as given in the batch calibration file. This estimated concentration is then validated, verifying this is within a set range of the actual concentration of the "level two" liquid control (also given in the batch calibration file). If an error has occurred, or if the estimated concentration is outside the expected range, the user is prompted to repeat the "level two" liquid control calibrator [1204]. Alternatively, the algorithm calculates updated calibration parameters as below [1205].

Generally, the calculation of liquid control updated 5-parameter log logistic parameters is carried out by the minimisation of error residuals.

Upon calculation of optimised calibration parameters, the batch calibration file is updated to include these parameters [1206], and the success of the liquid controls calibration adjustment algorithm is reported to the user [1207].

Quality Control Check

In particular embodiments of the present invention, the reader system incorporates an optical quality control algorithm. This algorithm compares the response from a quality control component scan with the expected response, and thereby validates the reader for the analysis of assays. This optical quality control may be required to be run at specific intervals, such as to ensure daily optical checking of the reader operation. Parameters for this optical self check are stored in the system's internal memory, and contain quality control verification parameters for the specific reader system, as determined during reader verification. This optical quality control data file comprises specific information, such as: quality control cartridge barcode identifier, scan positions of quality control features, and expected response range at each quality control feature. Data corresponding to this file may be encoded on a 2-D barcode on the quality control component, or encoded within an RFID chip associated with the quality control component. This data may be thereby read by the reader system, and stored in internal memory.

Figure 6:
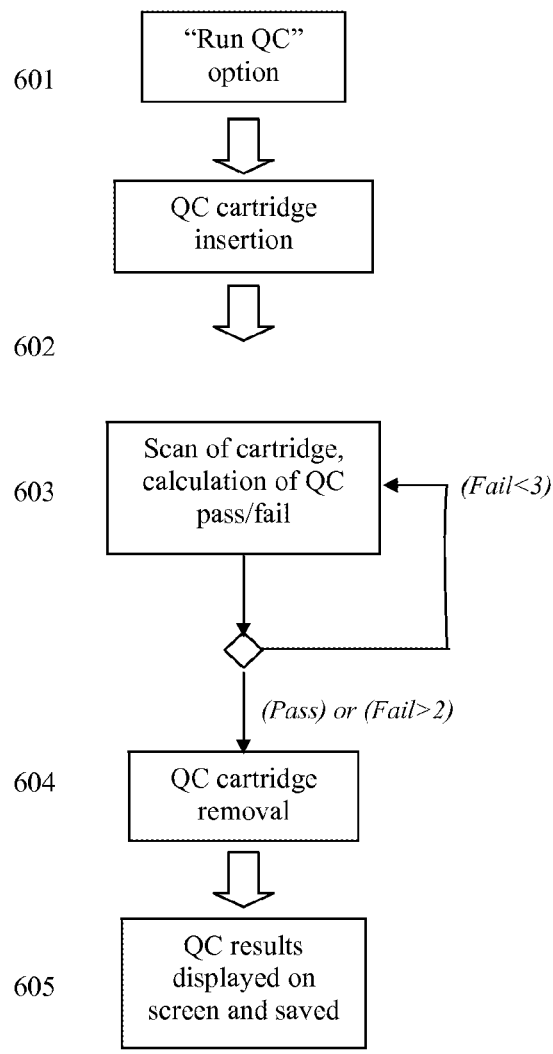
FIG. 6 shows a reader use procedure block diagram for a quality control scan.

In an exemplary embodiment of the present invention, a separate bar-coded optical quality control component is used and the optical self check procedure may be described as follows (as shown in FIG. 6): Upon initiation of the optical self check by the system operator [601] and insertion of the corresponding quality control device [602], the system checks the device barcode to ensure this corresponds with the quality control barcode stored in the quality control parameters file in memory. If this file do not exist, or if the cartridge is incorrect the check is halted.

The system then initiates a scan, recording the optical photoluminescence from the quality control cartridge according to the standard scan procedure [603]. The optical quality control algorithm examines the detected photoluminescence response at each of the defined quality control features scan positions and compares these responses to the expected response range at each quality control feature, respectively. If every response is within the expected response range, the quality control test is reported as a "pass". If any level falls outside these thresholds, the test is a failure, and the scan and tests are repeated. Scans and analyses are repeated up to three times. If one of these scans is a "pass", this is reported. If all these fail, the quality control test is reported as a "fail". The user is prompted to remove the QC cartridge [604]. Results are then displayed and scan details for the final scan are stored within reader memory [605], including: header details (such as: time/date, cartridge identifier, user identifier, scan parameters and final number of scans taken), a copy of the parameter file, the detailed "pass"/"fail" status for each quality control feature and original scan data.

Figure 10:
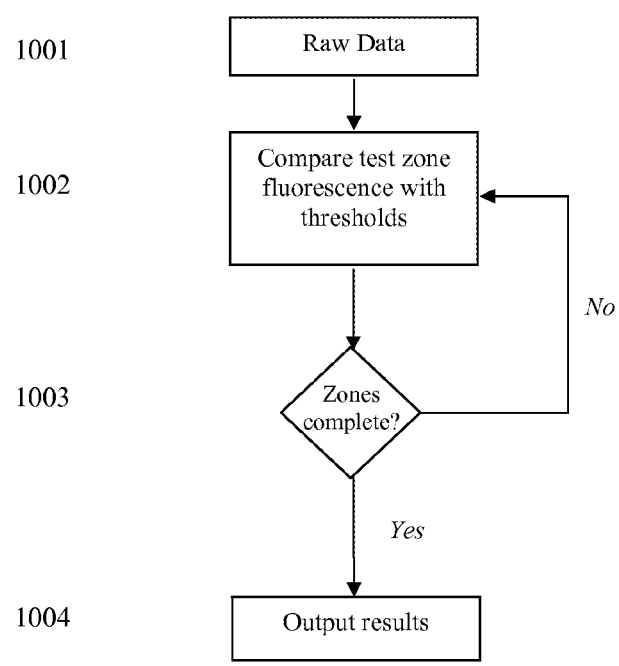
FIG. 10 shows a quality control algorithm block diagram.

The optical quality control algorithm is shown in FIG. 10, and may be summarised as follows: The algorithm takes as inputs the raw scan data [1001], and quality control parameters (as given in a quality control file, specific to the reader and quality control device). The algorithm records the detected photoluminescence response at a scan position nominated within the quality control data file. This position corresponds to defined quality control feature on the quality control device. Next, the algorithm compares the response to the expected response range for quality control feature [1002]. This range is specific to the feature, quality control device, and reader device; and is specified in the quality control data file. If the response is within this range, the optical setup is considered to be well aligned to this feature, and the result is a "pass". Otherwise, the quality control test is a "fail". This process is repeated for all features on all read channels of the quality control chip [1003]. The algorithm then outputs results corresponding to the "pass"/"ail" properties of each test [1004].

LED Feedback Control

In an embodiment of the present invention, the excitation source intensity is controlled through the measurement scan. This is carried out by monitoring the excitation source intensity using one or more dedicated photosensors. Active feedback of this intensity signal ensures that the emission power of the excitation source remains constant through the scan. This is important as changes in excitation source emission power lead to direct changes in assay photoluminescence which may create inaccuracies in measurements of analyte presence.

In an embodiment of the present invention, the reader has excitation sources being a bank of six similar LEDs. In this case, excitation power variation may be caused by, for example: power regulation variation, LED degradation over time, and thermal responses. Of these, a thermal response is particularly notable. As temperature increases or decreases linearly, the emission intensity of an LED decreases or increases exponentially, respectively. In this case, two sets of three LEDs each are optically isolated from each other using a baffle. A single photodiode is placed within each LED chamber, and monitors three corresponding LEDs. During the scan of a cartridge, only one LED in each isolated set of three LEDs is active at a specific time. Some portion of the emission from each LED is back-scattered or reflected from the aperture plate. This is monitored by the relevant photodiode. The LED emission power is thus detected by observing the photodiode signal. Monitoring and optimisation of the LED emission is carried out prior to the acquisition of assay luminescence, for each activation pulse of the corresponding LED. For example, optimisation of LED power may proceed for 25 ms, and then acquisition of assay luminescence may proceed for 15 ms for each scan data point. Alternatively, LED stabilisation may be carried out for each LED prior to the commencement of a scan, an LED applied voltage is maintained at the relevant stabilized setpoint for each LED throughout the scan.

Such optimisation of LED emission power is carried out as follows.

The applied voltage to each of the LEDs is individually controlled by the reader software. The voltage applied to each LED is optimised by the LED feedback algorithm to stabilise the optical emission power at an expected level. Initial levels for LED control voltages [1401] and expected phototransistor response for the desired LED emission power are stored in the reader calibration file for each LED.

Initially, the LED is set at the initial default voltage [1401], and the LED monitoring optical signal read [1402]. Optimisations of LED control voltages are calculated using a control algorithm, such as a proportional-integral controller, separately for each LED [1404].

Print-Out of Data

In an embodiment of the present invention, the reader system incorporates a printer [110] for the printout of hardcopies of scan results and associated audit data following the reading of an assay, or from stored memory. A typical sample print-out following a scan of a qualitative, six analyte, drugs of abuse panel is shown in FIG. 13. Additional printable data may include: user lists, reader settings, events or error logs, installed calibrations, or quality control results.

In an embodiment of the present invention, touch-sensitive screen elements may be provided on the touchscreen interface [102] which initiate the printing of data, or the feeding of paper through the printer. Further, prompts may be provided on screens in the user interface containing printable material. These prompts inform the user that these touch-sensitive screen elements may be used to initiate printing of data.

System Self-Check

In embodiments of this invention, the reader incorporates software and electronics for the initiation and interpretation of self-check tests. Generally, these tests may be initiated automatically at start up of the reader device, or initiated by selection of user interface options by the user. Upon initiation of the self-check, the reader verifies the operation of various internal and peripheral components. For example, verification may be carried out on memory devices, wireless communications, port connections, motor operation, various control sub-systems, excitation sources and detectors, printer operation, internal and external barcode sensors, battery operation, and power supply operation.

Further connectivity may be provided for password protected access to device test menus incorporating these and further test operations. These may aid an engineer in the identification and resolution of errors occurring in device operation.

Upon encountering an error, this may be reported to the user, and a detailed report included in an internal events or error log file. The reader may also be prevented from initiating tests while components have been found to be in an error state. Further reader functionality may be likewise restricted should associated components be detected to be in an error state.

Security

In embodiments of the present invention, various strategies may be provided to achieve security of data. For example, various user access levels may be provided; each with specific levels of data access and control rights. One implementation of the current invention has two access levels, being "administrator" and "user". Generally, the "user" level has a subset of the "administrator" level rights. Specifically; scan, quality control, calibration, record review and printing functionality is available to all operators. In addition to these rights, the "administrator" level operator has access to additional functionality, including the transfer of records to external devices, deletion of records, initiating of firmware or software updates, and setting of reader options. In an embodiment of the present invention, the "administrator" level user can create and manage user accounts, set requirements for entering passwords at log-on, and further set these passwords for each user.

In an embodiment of the present invention, event audit logs are maintained of all settings changes, scans and system warnings and errors. Each system event is uniquely identifiable, and is linked to the time of the event, and the user logged into the device.

In an embodiment of the present invention, batch calibration files may only be acquired from specific secure, non-rewritable chips. These calibration files may be encoded, to prevent interpretation outside the reader device.

In an embodiment of the present invention, connectivity to the reader, and access to reader connection menus may be further password controlled. Wireless connections from the reader device may require setup using the reader user interface by an "administrator" level user.

Reader Settings

In embodiments of the present invention, the reader user interface provides settings sub-menus which enable an "administrator" level user to set or modify various reader settings and parameters. These may include: configuration of user IDs and passwords; requirements for, or required frequency of, optical quality control or liquid control scans for the running of test scans; language settings; display brightness; configuration of functions enabling the reader timing of assay development, and subsequent automatic initiation of scans; setting of wireless connections and settings; handling of error reports; volume levels of integrated speakers; management and/or deletion of saved results and calibrations; or activation of ports and data communication settings.

Memory and Files

In embodiments of the present invention, the reader system incorporates memory and a file management system for the storage of essential data, operation parameters, and software and user interface details. Files stored within this memory may include: Scan files, calibration files, quality control run files, user lists, settings and change logs, scan logs, calibration run logs, or user logs. In order to review a potentially large volume of scan files, search functionality may be implemented. This allows the user to filter scans results by date, operator, patient ID or test. Generally, original scan data and calibration parameters are included in each scan results file, in addition to salient reader information for quality control of scans.

In a particular embodiment of the present invention, the reader system may store five thousand patient scan records in internal memory, with the oldest records being deleted once new ones are taken.

EXAMPLES

The following examples serve to further illustrate the methods and devices of the present disclosure. These examples are in no way intended to limit the scope of the invention.

Example 1: Six Channel Fluorescence Reader System

This example describes an example reader system for the recording and interpretation of fluorescence from immunoassays, according to the present invention. This reader system receives a cartridge, comprising six vertical channels. Each channel comprises an immunoassay configured for the detection of a specific analyte within a single fluid sample. The reader system captures fluorescence from the surface of each immunoassay, quantifies the fluorescent response the single capture zone of each immunoassay, and determines a quantitative or qualitative measurement each analyte's presence within said sample.

Figure 2:
FIGS. 2(a) and 2(b) show reader system casing diagrams: (a) side A and (b) side B.
Figure 2:
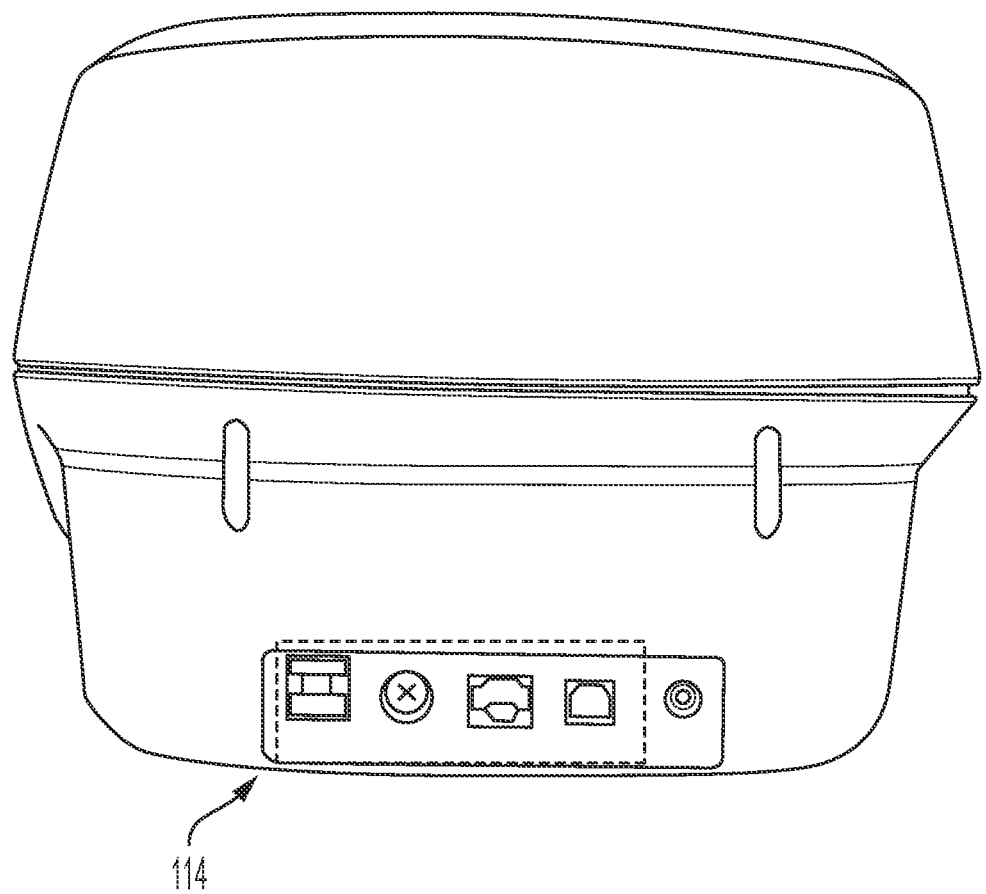
Figure 3:
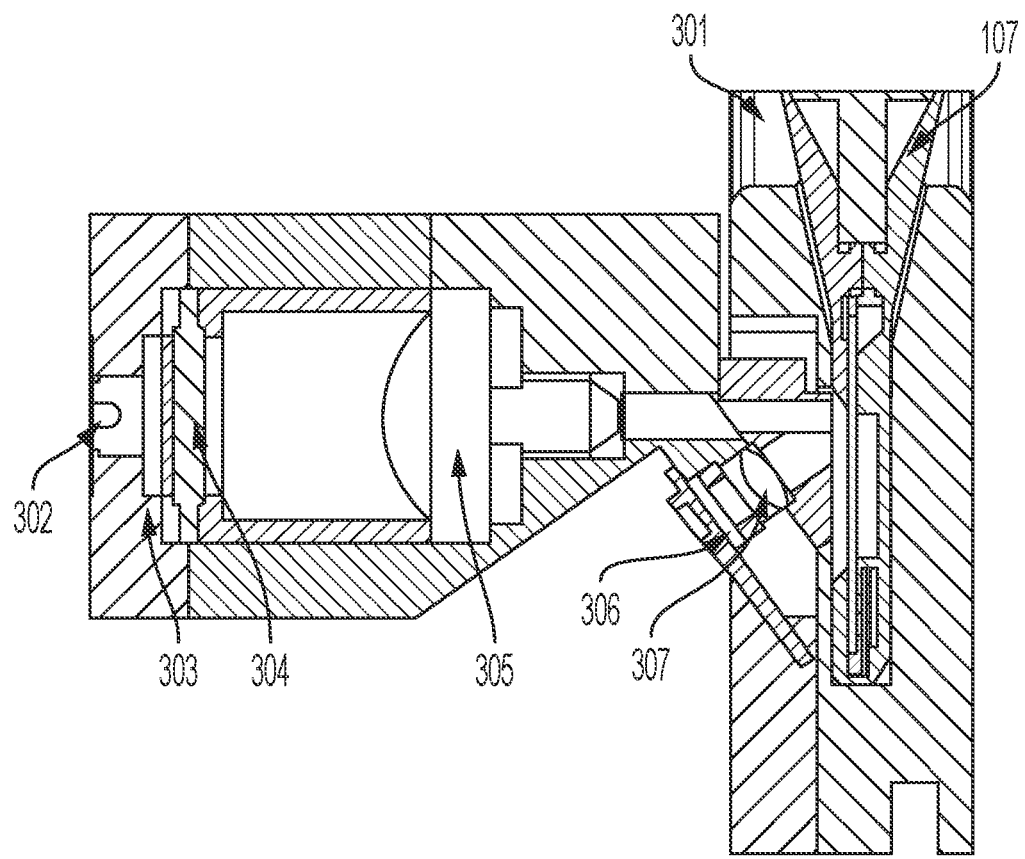
FIGS. 3(a) and 3(b) show reader optics diagrams.
Figure 3:
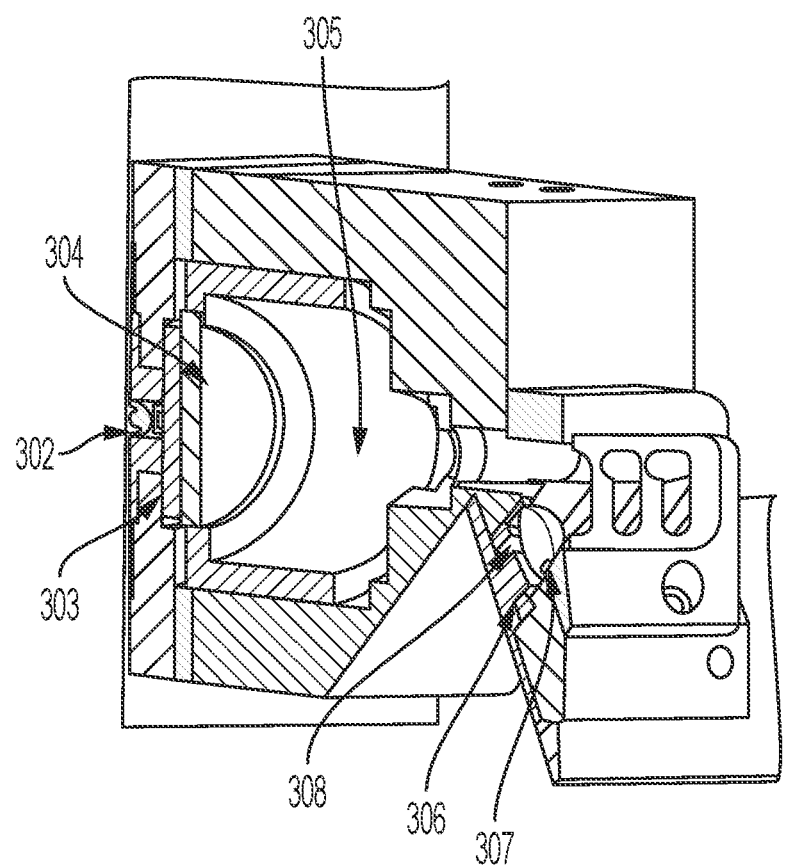

A system diagram of the reader is shown in FIG. 1. In addition, a diagram of the reader and the reader's optical components are shown in FIGS. 2 and 3, respectively. In brief, the reader system comprises a casing [204], incorporating a touch-screen display and data entry device [102] an on/off switch [101], a multicolor status indicator light [202] and a device access port with rotating lid [201]. The casing contains a holster receptacle [301] for receiving an external immunoassay device [107]. Further, the reader comprises an optical system within the casing, consisting of excitation and collection optics within a single optical block; and an electromechanical motor system, such as a stepper motor, whereby the holster is moved with respect to the optical block [106].

Also, the reader system incorporates digital processors [104] and electronics for the actuation and control of readings, and non-volatile digital memory for the storing of data [105]. Finally, the reader incorporates communication ports and wireless connectivity [114], a power management system [113], an internal battery [111] and an external thermal printer [124] for the printout of hardcopies of scan results following the reading of an assay, or from stored memory. This printer interfaces with and is powered by the reader via a communication port.

With regard to the particulars of the reader assembly and components, these are further detailed, below.

Within the cartridge holster [301], spring loaded dowels are located in positions corresponding to recesses in the assay cartridge when the cartridge is correctly localised within the holster. Upon correct insertion of the cartridge, the dowels register with the recessed features of the cartridge. This locks the cartridge in position, ensuring assays are localised at the optical plane until a force is applied to remove said cartridge. Also, physical alignment features prevent the mis-insertion of the cartridge, by blocking insertion of the cartridge at an incorrect rotational alignment.

The reader incorporates optical and mechanical sensors, which register full cartridge insertion and removal. These sensors are held within the cartridge holster, and their positioning corresponds to locations which define the cartridge insertion or removal of the cartridge. In this case, the optical sensor is a light source and photosensor couple. This is be located in close proximity to the mouth of the holster. Upon insertion, the cartridge blocks propagation of light from the sensor light source to its corresponding photosensor. The sensor registers full removal of the cartridge by the resumption of light propagation from the sensor light source to its corresponding photosensor. A mechanical switch sensor is located at the base of the holster. Upon full insertion of the cartridge into the holster, this switch is actuated by the cartridge, enabling the detection of cartridge insertion.

The motor component integrates an encoder system which detects and reports the relative motor actuation position. Holster position may be determined with reference to this signal and signals received from particular optical travel sensors [120a] located relative to specific positions in the holster travel. The holster component incorporates beam blocking features, which break an optical beam sensed by the optical travel sensors, indicating holster position at these locations.

The reader system incorporates an internal 2D barcode camera system [120] for the reading of barcode information encoded on the cartridge. This camera system further incorporates a light source for illumination of the barcode within the reader.

The excitation optics within the optical block include: six light sources [302], an aperture plate [303], an interference filter [304], and a single excitation lens [305].

Light sources consist of surface mounted device LEDs, each with an integrated lens which serves to partially collimate emitted light [302]. The LEDs have an optical emission wavelength of circa 606 nm (LOE63B; Osram GmBH). The aperture plate is a thin flat metal shim, etched with six rectangular optical apertures which restrict excitation light rays to those passing through the aperture [303]. Each aperture is aligned to emission from a single LED. In the reader system, apertures are 0.7 mm-0.8 mm in width and 0.3-0.4 mm in height, and each excitation area is 1.2 mm in width and 0.6 mm in height.

The excitation filter [304] is located within the light paths of excitation and centred within these light paths using a tube construction system. The optical excitation filter shapes the spectral profile of excitation light experienced by the immunoassay device. This filter acts to ensure spectral separation between excitation light and photoluminescent label emitted light. An optical excitation filter may, for example, be of band-pass or short-pass variety, and may operate by interference or absorptive mechanisms. Generally, the excitation filter is selected such that the filter pass-band corresponds to some portion of the excitation spectrum of the photoluminescent label, and that the filter stop-band corresponds to some portion of the emission spectrum of the photoluminescent label. The Stokes' shift between the photoluminescent label's excitation and emission spectra defines the maximum filter transition band. In this case, a band-pass interference optical filter is selected, with a central pass wavelength of 590 nm, and a transparent bandwidth of 60 nm (BK-590-60; Interferenzoptik GmbH).

The excitation lens [305] is located within the light paths of excitation and centred within these light paths using a tube construction system. This lens directs light source emitted optical energy to the surface of the immunoassay device. The lens is biconvex aspheric in design, and is formed of transparent cyclic olefin co-polymer material (Zeonex 480 R).

Generally, the light sources have emission wavelengths compatible with the excitation spectra of photoluminescent labels associated with the mobilizable or control reagents of the assay. Such labels may include dark red emitting fluorophores, such as DyLight® 650 (Thermo-Fischer Scientific), Alexa Fluor® 647 (Invitrogen Corporation) or Cy5.

Collection optics within the optical block include: six collection lenses [307], a glass absorptive filter [308] and six photodiodes for the detection and quantification of this luminescence [306]. Each collection lens [307] collects light from an individual excitation area, an area of the immunoassay surface illuminated by the excitation optical assembly; and directs this light towards the central portion of a corresponding photodiode [306]. All six lenses are identical in design, being biconvex aspheric, and are formed of transparent cyclic olefin co-polymer material (Zeonex 480 R). A single long-pass glass absorptive optical filter [308] is used to filter excitation light from all channels. This filter has optical pass-band beyond a wavelength of ca. 665 nm (ZVLO50; Knight Optical (UK) Ltd.). This filters out residual reflected or scattered excitation light, and passes light associated with fluorescence of the labelled conjugates.

There is an angular offset between the plane of optical collection paths of the collection optics, and the plane of optical excitation paths of the excitation optics; with the optical excitation plane is normal to the cartridge surface, while detection is offset by 35 degrees. The angular position of these planes and their specific offset are selected in order to inhibit direct reflection of excitation light into the detector assembly.

The reader system incorporates digital processors and electronics for the actuation and control of readings. Generally an operations processor [104a] controls time critical sensing and control operations, such as the operation of motors, optical electronic components, sensors, and scan processing. An additional interface processor controls display and interface components, interpreting data entry and communications protocols. Additionally, this processor control internal digital memory [105]; enabling the writing, reading, search and transfer of data.

The reader system incorporates non-volatile digital memory for the storing of data [105]. Generally, such data includes collected scan data, and corresponding patient details and assay results; user details and passwords; events and error logs; calibration parameters; reader settings; user interface screens; interface and communications parameters; and reader operation programs. This memory consists of: internal flash memory and an internal SD-card.

The reader system incorporates communications ports [114]. In particular, components and protocols are incorporated for wired connectivity, including USB, and Ethernet. These facilitate communication to, and control of devices external to the reader. Specifically, this connectivity enables remote diagnostics, firmware or software updates and data transfer, and control of an external barcode reader device [115]. The reader also includes components and protocols for external wireless access by WI-FI. Specifically, this connectivity enables remote diagnostics, firmware or software updates and data transfer.

The reader system incorporates an external thermal printer [124] for the printout of hardcopies of scan results and associated audit data following the reading of an assay, or from stored memory. This printer is communicates and is powered by the reader via a connection to one of the readers communication ports [114]. The reader system is portable, being intended for bench- or table-top point-of-care use, and includes an internal battery [111], which can power the reader in situations where the system is not connected to a power supply [112]. This battery is rechargeable, and recharges while the reader is connected to a mains power supply. A power system [113] monitors battery charge, reporting this to the user, and regulating such details as: charge speed, battery temperature, and minimum charge levels before the unit is automatically shut down.

In some embodiments, an SD card component holds assay specific calibration data relating to an assay cartridge batch. The SD card may be introduced into a reader system socket, and the assay specific calibration data copied to internal reader memory. SD card devices are of a secure write-once, read many times form. Additionally, a standard SD may be inserted into the SD slot, and the user may transfer saved data (such as scans, results, settings, calibrations or quality control data) from the internal device to the SD card for back up or subsequent transport.

With regard to system control, the LED emission timings and photodiode read timings are tuned such that only one test is being excited at a specific time, ensuring that optical crosstalk between channels is minimised. Further, the LED emission intensity for each LED is stabilized to a standard setpoint prior to the commencement of each scan through the measurement scan. This is carried out by monitoring the excitation source intensity using two dedicated photodiodes. Active feedback of this intensity signal ensures that the emission of the excitation source remains constant across all scans.

Also, prior to each LED emission pulse, the reader system also records a dark count, corresponding to detected signal without activation of the corresponding LED. This is integrated over an equivalent time to the LED pulse time. Following the recording of all scan points, the received signals are corrected by subtraction of each dark count from that acquired during activation of the corresponding LEDs. This enables compensation for light leakage into the device, interference from light generation within the device, or thermal or electronic noise. The reader includes an algorithm for the detection of optical emission peaks from each optical scan. Algorithm parameters may include such details as expected numbers of peaks, expected peak scan positions, expected widths of peaks, expected ranges of peak heights. The peak detection algorithm includes background subtraction; compensating for background fluorescence derived from the assay materials, stray background light, unbound labelled assay materials or other sources. This is realised by estimation and subtraction of background fluorescence at the point of the peak maximum. Such estimation is carried out by registering fluorescence levels at particular scan positions at a defined distance to either side of the peak position, then determining a linear fit to the background versus scan position, and then estimation of the level of background fluorescence at a scan position at a position corresponding to the peak maximum.

Sets of quality controls are actualised in software to verify that an assay panel ran in a defined manner. These include: quality control check of scan data, including a check of control line development, a check of channel clearance, and checks as to the size and position of peaks. Additionally, the software verifies the time of test as being within the expiry data of a particular assay. In particular, the level of detected luminescence is characterised at a particular scan position, defined in calibration parameters for the assay in question, at which no capture or control zones are present, and which generally corresponds to background fluorescence. If this luminescence is found to be above a certain level defined in calibration parameters for the assay in question, the unbound luminescent materials is not taken to have achieved full clearance, and the particular assay is termed a "Missrun". Control zone peaks are further analysed: if these are not found, or are of insufficient magnitude, the assay is likewise is considered to have not fully developed, and is likewise termed a "Missrun".

The reader includes a calibration algorithm for the qualification or quantification of luminescence from active areas of an assay scan. This algorithm takes as input the following: calibration parameters specific to the assay batch and peak heights as determined by a peak detection algorithm for each of the capture and control zones. For each analyte, the algorithm processes the corresponding capture zone peak height, according to the calibration parameters. Generally for qualitative tests, the algorithm compares the peak height versus a threshold value, and reports a positive or negative result. Alternatively for quantitative tests, the algorithm characterises the concentration of an analyte within the test sample, according to assay specific calibration parameters. Should the estimated concentration be outside the assay's bounds of quantization, the algorithm reports that the concentration is greater than or less than particular limits of quantization, respectively.

A physically separate quality control component [108], of external dimensions similar to that of the assay cartridge is incorporated. This component incorporates materials exhibiting specific, characterised levels of fluorescence. The quality control component's fluorescent areas are defined using masked fluorescent PVC materials. The quality control component's fluorescent areas may be localised at the optical plane within the reader. Fluorescent areas are patterned in a defined manner, such that optical misalignments lead to predictable changes in scan responses. A processing algorithm for the analysis of quality control component scans is incorporated in the reader. This algorithm compares expected responses from fluorescent areas with those of received responses, and validates the reader for the analysis of assays.

The reader also includes a processing algorithm for the verification of assay batch responses or optionally, the updating of assay specific calibration parameters to compensate for assay based changes in response. This algorithm analyses the response of one or more assay cartridges of the specified batch run with control liquids of specified concentrations. Assay responses are verified to be within expected limits. Additionally, internal calibration parameters may then be updated to provide a best-fit result to control responses.

We claim:

1. A system comprising a reader for analyzing one or more analytes in a fluid sample, the reader comprising:
    a casing comprising at least one port into which a cartridge comprising an immunoassay device with multiple parallel immunoassay channels may be inserted;
    a holster which receives and positions the cartridge within the reader;
    an optical system comprising:
        excitation optics comprising multiple light sources and an excitation lens to direct light from each one of the multiple light sources to a corresponding individual excitation area upon a different immunoassay channel when the cartridge is positioned within the holster; and
        collection optics comprising multiple photosensors and a collection lens to collect light emitted from each one of the individual excitation areas and direct the collected light towards a corresponding photosensor;
    an electromechanical motor system to move the holster, with the cartridge positioned therein, to interrogate different regions along each of the multiple immunoassay channels; and
    one or more digital processors and associated electronics to receive data from and control the optical and electromechanical motor systems,
    wherein the casing contains the holster, the optical system, the electromechanical motor system and the one or more digital processors and associated electronics.

2. The system of claim 1, wherein:
    the casing comprises a bottom on which the reader rests and a top opposite to the bottom and comprising the port, and
    the port leads to the holster, which is oriented in a vertical direction, directed from the port at the top of the casing down, towards, and substantially perpendicular to, the bottom of the casing.

3. The system of claim 2, comprising, the cartridge within such that the multiple immunoassay channels are oriented substantially along the vertical direction.

4. The system of claim 1, wherein the reader further comprises memory for storing data including reader operation programs, and wherein the memory:
    is in communication with the one or more digital processors,
    comprises a batch calibration file comprising positions and numbers of the immunoassay channels of the cartridge to be inserted into the reader, and
    causes modification of excitation and read logic to cause the one or more digital processors of the reader to tune light source emission and photon sensor read timings in accordance with the positions and numbers of the immunoassay channels.

5. The system of claim 4, wherein the modified excitation and read logic causes the one or more digital processors of the reader to act to only excite and read from immunoassay channels that are present in the immunoassay device of the cartridge.

6. The system of claim 4, wherein the emission timings of the light sources and the photosensor read timings are tuned such that only one test is being excited at a specific time.

7. The system of claim 4, wherein the emission timings of the light sources and the photosensor read timings are tuned such that multiple, but spatially separated, immunoassay channels are illuminated and read simultaneously.

8. The system of claim 4, wherein the memory comprises operation parameters and software that cause the one or more digital processors to collect scan data generated when the optical system scans the vertically oriented immunoassay device.

9. The system of claim 8, wherein the collected scan data comprises data corresponding to optical energy collected by a particular one of the multiple photosensors at points of a scan along a particular one of the multiple immunoassay channels that corresponds to the particular photosensor.

10. The system of claim 8, wherein the memory comprises a calibration file that provides peak recognition parameters for detection of optical emission peaks within the scan data.

11. The system of claim 1, further comprising the cartridge, wherein the cartridge is positioned within the holster, and wherein a surface of the cartridge comprising the multiple immunoassay channels is localised at an optical plane such that each light source transmits light to a particular one of the individual excitation areas on a different one of the immunoassay channels.

12. The system of claim 11, wherein assays of each of the multiple immunoassay channels of the cartridge are developed, the cartridge having been left for sufficient time for the assays to develop prior to insertion into the reader.

13. A system comprising a reader for analyzing one or more analytes in a fluid sample and a cartridge comprising an immune assay device with multiple parallel immunoassay channels, the reader comprising:
    a holster in which the cartridge is positioned;
    an optical system comprising:
        excitation optics comprising multiple light sources and an excitation lens that directs light from each one of the multiple light sources to a corresponding individual excitation area upon a different immunoassay channel of the cartridge; and
        collection optics comprising multiple photosensors and a collection lens that collects light emitted from each one of the individual excitation areas and direct the collected light towards a corresponding photosensor; and
    an electromechanical motor system to move the holster, with the cartridge positioned therein, to interrogate different regions along each of the multiple immunoassay channels.

* * * * *

UNITED STATES PATENT AND TRADEMARK OFFICE
CERTIFICATE OF CORRECTION

| | | |
|---|---|---|
| PATENT NO. | : 12,379,317 B2 | Page 1 of 1 |
| APPLICATION NO. | : 17/465049 | |
| DATED | : August 5, 2025 | |
| INVENTOR(S) | : Shane Moynihan et al. | |

It is certified that error appears in the above-identified patent and that said Letters Patent is hereby corrected as shown below:

In the Claims

At Column 30, Lines 52-54 (Claim 3), please delete:
"the cartridge within such that the multiple immunoassay channels are oriented substantially along the vertical direction."

And insert:
--"the cartridge within the holster such that the multiple immunoassay channels are oriented substantially along the vertical direction."--

Signed and Sealed this
Twenty-first Day of October, 2025

John A. Squires
*Director of the United States Patent and Trademark Office*